US008409581B2

(12) United States Patent
Mandler et al.

(10) Patent No.: US 8,409,581 B2
(45) Date of Patent: Apr. 2, 2013

(54) COMPOUNDS FOR TREATING AMYLOIDOSES

(75) Inventors: Markus Mandler, Vienna (AT); Radmila Santic, Vienna (AT); Harald Weninger, Vienna (AT); Edith Kopinits, Landegg (AT)

(73) Assignee: Affiris AG, Vienna (AT)

( * ) Notice: Subject to any disclaimer, the term of this patent is extended or adjusted under 35 U.S.C. 154(b) by 0 days.

(21) Appl. No.: 12/997,673

(22) PCT Filed: Jun. 12, 2009

(86) PCT No.: PCT/AT2009/000235
§ 371 (c)(1),
(2), (4) Date: Dec. 13, 2010

(87) PCT Pub. No.: WO2009/149485
PCT Pub. Date: Dec. 17, 2009

(65) Prior Publication Data
US 2011/0171243 A1    Jul. 14, 2011

(30) Foreign Application Priority Data
Jun. 12, 2008    (AT) .................................. A 952/2008

(51) Int. Cl.
*A61K 39/00*    (2006.01)
*A61K 38/08*    (2006.01)
*C07K 7/06*    (2006.01)
(52) U.S. Cl. ..................... 424/185.1; 530/328
(58) Field of Classification Search ............... 424/185.1; 530/326, 327, 328
See application file for complete search history.

(56) References Cited

U.S. PATENT DOCUMENTS

| | | | |
|---|---|---|---|
| 7,504,490 B1 * | 3/2009 | Weinstock et al. | .......... 536/23.1 |
| 2004/0067535 A1 | 4/2004 | Kim et al. | |
| 2006/0111301 A1 | 5/2006 | Mattner | |
| 2009/0004210 A1 | 1/2009 | Mattner et al. | |

FOREIGN PATENT DOCUMENTS

| | | | |
|---|---|---|---|
| EP | 1440981 A2 * | 7/2004 | |
| WO | WO 00/72880 A2 | 12/2000 | |
| WO | WO 2004/062556 A2 | 7/2004 | |
| WO | WO 2006/005707 A2 | 1/2006 | |
| WO | WO 2006/045037 A2 | 4/2006 | |
| WO | WO 2007068412 A2 * | 6/2007 | |

OTHER PUBLICATIONS

Janus C et al. Abeta peptide immunization reduces behavioural impairment and plaques in a model of Alzheimer's disease. Nature, 2000; 408:979-982.*
Morgan D et al. Abeta peptide vaccination prevents memory loss in an animal model of Alzheimer's disease. Nature, 2000; 408:982-985.*
Putnam NH et al. The amphioxus genome and the evolution of the chordate karyotype. Nature, Jun. 19, 2008; 453(7198):1064-71.*
Schenk D et al. Immunization with amyloid-beta attenuates Alzheimer-disease-like pathology in the PDAPP mouse. Nature, 1999; 400:173-177.*
Solomon B. Immunological approaches as therapy for Alzheimer's disease. Expert Opin. Biol. Ther. 2002; 2(8):907-917.*
Vickers JC. A vaccine against Alzheimer's disease—Developments to date. Drugs Aging. 2002; 19(7):487-494.*
Krishnamurthy PK & Sigurdsson EM. (2011) Therapeutic applications of antibodies in non-infectious neurodegenerative diseases. New Biotechnol. 28(5):511-517.*
James A. R. Nicoll, et al., "Neuropathology of human Alzheimer disease after immunization with amyloid-β peptide: a case report", Nature Medicine, vol. 9, No. 4, Apr. 2003, pp. 448-452.
A. J. Bayer, et al., "Evaluation of the safety and immunogenicity of synthetic Aβ42 (AN1792) in patients with AD", Neurology, vol. 64, Jan. 2005, pp. 94-101.
James A. R. Nicoll, et al., "Aβ Species Removal After Aβ$_{42}$ Immunization", J. Neuropathol. Exp. Neurol., vol. 65, No. 11, Nov. 2006, pp. 1040-1048.
William G. T. Willats, "Phage display: practicalities and prospects", Plant Molecular Biology, vol. 50, 2002, pp. 837-854.
Petra Burgstaller, et al., "Aptamers and aptazymes: Accelerating small molecule drug discovery", Current Opinion in Drug Discovery & Development, vol. 5, No. 5, 2002, pp. 690-700.
Michael Famulok, et al., "Nucleic Acid Aptamers—From Selection in Vitro to Applications in Vivo", Accounts of Chemical Research, vol. 33, No. 9, 2000, pp. 591-599.
Günter Mayer, et al., "Controlling small guanine-nucleotide-exchange factor function through cytoplasmic RNA intramers", PNAS, vol. 98, No. 9, Apr. 24, 2001, pp. 4961-4965.
Manmohan Singh, et al., "Advances in vaccine adjuvants", Nature Biotechnology, vol. 17, Nov. 1999, pp. 1075-1081.
Derek T. O'Hagan, et al., "Recent Advances in the Discovery and Delivery of Vaccine Adjuvants", Nature Reviews, Drug Discovery. vol. 2, Sep. 2003, pp. 727-735.
International Search Report issued Apr. 8, 2010, in International application No. PCT/AT2009/000235.
2nd Office Action issued Apr. 2, 2009, In Austria Patent Application No. 4A A 952/2008-2 (with English translation).
Alex E. Roher, et al., "Amyloid beta peptides in human plasma and tissues and their significance for Alzheimer's disease", Alzheimer's & Dementia, vol. 5, No. 1, The Journal of the Alzheimer's Association, (Elsevier), XP002572893, Jan. 1, 2009, pp. 18-29.

(Continued)

*Primary Examiner* — Elizabeth C Kemmerer
*Assistant Examiner* — Kimberly A Ballard
(74) *Attorney, Agent, or Firm* — Oblon, Spivak, McClelland, Maier & Neustadt, L.L.P.

(57) ABSTRACT

The present invention relates to the use of mimotopes in the treatment of β-Amyloidoses including but not limited to Alzheimer's disease, whereby said mimotopes are able to induce the in vivo formation of antibodies directed to non truncated Aβ1-40/42, and N-terminally truncated forms AβpE3-40/42, Aβ3-40/42, Aβ11-40/42, AβpE11-40/42 and Aβ14-40/42 without interfering with physiological functions of APP signalling.

4 Claims, 7 Drawing Sheets

OTHER PUBLICATIONS

Marcus Mandler, et al., "The Mimovax Vaccine: A Novel Alzheimer Treatment Strategy Targeting Truncated Aβ40/42 by Active Immunization", Alzheimer's & Dementia, vol. 5, No. 4, The Journal of the Alzheimer's Association, XP026253365, Jul. 1, 2009, p. 114.

Achim Schneeberger, et al., "Development of Alzheimer AFFITOPE vaccines—from concept to clinical testing", Alzheimer's & Dementia, vol. 5, No. 4, The Journal of the Alzheimer's Association, XP026220250, Jul. 1, 2009, p. 257.

J.-M. M., "Vaccin anti-Alzheimer", Revue Francophone Des Laboratoires, vol. 2008, No. 400, XP022667610, Jan. 1, 2008, p. 14.

Affiris AG: "Alzheimer Impfung", (Internet Citation), Mar. 9, 2010, XP002572894, Retrieved from the Internet: www.affiris.com/html/de/imfstoffe/morbus_alzheimer_interessierte_impfung.html>, 5 pages.

Yuan Shi, et al., Quantitative determination of the topological propensities of amyloidogenic peptides, Biophysical Chemistry, 120, 2006, pp. 55-61.

* cited by examiner

```
                        SEQUENCE LISTING

<160> NUMBER OF SEQ ID NOS: 154

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 1

Ser His Thr Arg Leu Tyr Phe Cys
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 2

Ser Gly Glu Tyr Val Phe His Cys
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 3

Ser Gly Gln Leu Lys Phe Pro Cys
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 4
```

```
Ser Gly Gln Ile Trp Phe Arg Cys
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 5

Ser Gly Glu Ile His Phe Asn Cys
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 6

Gly Gln Ile Trp Phe Ile Ser Cys
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 7

Asn Asp Ala Lys Ile Val Phe Cys
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 8

Gly Gln Ile Ile Phe Gln Ser Cys
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 9

Gly Gln Ile Arg Phe Asp His Cys
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
                         mimotope sequence

<400> SEQUENCE: 10

His Met Arg Leu Phe Phe Asn Cys
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 11

Gly Glu Met Trp Phe Ala Leu Cys
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 12

Gly Glu Leu Gln Phe Pro Pro Cys
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 13

Gly Glu Leu Trp Phe Pro Cys
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 14

Ser His Gln Arg Leu Trp Phe Cys
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 15

His Gln Lys Met Ile Phe Ala Cys
1               5

<210> SEQ ID NO 16
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 16

Gly Glu Met Gln Phe Phe Ile Cys
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 17

Gly Glu Leu Tyr Phe Arg Ala Cys
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 18

Gly Glu Ile Arg Phe Ala Leu Cys
1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 19

Gly Met Ile Val Phe Pro His Cys
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 20

Gly Glu Ile Trp Phe Glu Gly Cys
1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 21

Gly Glu Ile Tyr Phe Glu Arg Cys
1               5
```

```
<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 22

Ala Ile Pro Leu Phe Val Met Cys
1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 23

Gly Asp Leu Lys Phe Pro Leu Cys
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 24

Gly Gln Ile Leu Phe Pro Val Cys
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 25

Gly Glu Leu Phe Phe Pro Lys Cys
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 26

Gly Gln Ile Met Phe Pro Arg Cys
1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence
```

```
<400> SEQUENCE: 27

His Met Arg Met Tyr Phe Glu Cys
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 28

Gly Ser Leu Phe Phe Trp Pro Cys
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 29

Gly Glu Ile Leu Phe Gly Met Cys
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 30

Gly Gln Leu Lys Phe Pro Phe Cys
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 31

Lys Leu Pro Leu Phe Val Met Cys
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 32

Gly Thr Ile Phe Phe Arg Asp Cys
1               5

<210> SEQ ID NO 33
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      mimotope sequence

<400> SEQUENCE: 33

Thr His Gln Arg Leu Trp Phe Cys
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 34

Gly Gln Ile Lys Phe Ala Gln Cys
1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 35

Gly Thr Leu Ile Phe His His Cys
1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 36

Gly Glu Ile Arg Phe Gly Ser Cys
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 37

Gly Gln Ile Gln Phe Pro Leu Cys
1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 38

Gly Glu Ile Lys Phe Asp His Cys
1               5
```

```
<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 39

Gly Glu Ile Gln Phe Gly Ala Cys
1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 40

Gln Leu Pro Leu Phe Val Leu Cys
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 41

His Gln Lys Met Ile Phe Cys
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 42

Gly Glu Leu Phe Phe Glu Lys Cys
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 43

Gly Glu Ile Arg Phe Glu Leu Cys
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence
<220> FEATURE:
<223> OTHER INFORMATION: N-term Ac
```

```
<400> SEQUENCE: 44

Gly Glu Ile Tyr Phe Glu Arg Cys
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 45

Ser Gly Glu Ile Tyr Phe Glu Arg Cys
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 46

Ala Gly Glu Ile Tyr Phe Glu Arg Cys
1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 47

Cys Gly Glu Ile Tyr Phe Glu Arg
1               5

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 48

Asp Ala Glu Phe Arg His Asp Ser Gly Tyr Cys
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 49

Cys His Gln Lys Leu Val Phe Phe Ala Glu Asp
1               5                   10

<210> SEQ ID NO 50
<211> LENGTH: 10
<212> TYPE: PRT
<213> ORGANISM: Artificial Sequence
```

```
-continued

<220> FEATURE:
<223> OTHER INFORMATION: Description of Artificial Sequence: Synthetic
      mimotope sequence
<220> FEATURE:
<221> NAME/KEY: MOD_RES
<222> LOCATION: (1)..(1)
<223> OTHER INFORMATION: Pyroglutamate

<400> SEQUENCE: 50

Glu Val His His Gln Lys Leu Val Phe Cys
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 51

Glu Val His His Gln Lys Leu Val Phe Cys
1               5                   10

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 52

Cys Gly Leu Met Val Gly Gly Val Val
1               5

<210> SEQ ID NO 53
<211> LENGTH: 40
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 53

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
            35                  40

<210> SEQ ID NO 54
<211> LENGTH: 42
<212> TYPE: PRT
<213> ORGANISM: Artificial Sequence
<220> FEATURE:
<223> OTHER INFORMATION: Description of Artificial Sequence: Synthetic
      mimotope sequence

<400> SEQUENCE: 54

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
            35                  40
```

```
<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope sequence
<220> FEATURE:
<221> NAME/KEY: MOD_RES
<222> LOCATION: (1)..(1)
<223> OTHER INFORMATION: Ser, Ala, Cys or not present
<220> FEATURE:
<221> NAME/KEY: MOD_RES
<222> LOCATION: (3)..(3)
<223> OTHER INFORMATION: Ser, Thr, Glu, Asp, Gln or Met
<220> FEATURE:
<221> NAME/KEY: MOD_RES
<222> LOCATION: (4)..(4)
<223> OTHER INFORMATION: Ile, Tyr, Met or Leu
<220> FEATURE:
<221> NAME/KEY: MOD_RES
<222> LOCATION: (5)..(5)
<223> OTHER INFORMATION: Leu, Arg, Gln, Trp, Val, His, Tyr, Ile, Lys,
      Met or Phe
<220> FEATURE:
<221> NAME/KEY: MOD_RES
<222> LOCATION: (7)..(7)
<223> OTHER INFORMATION: Ala, Phe, His, Asn, Arg, Glu, Ile, Gln, Asp,
      Pro, Trp or Gly
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: May or may not be present

<400> SEQUENCE: 55

Xaa Gly Xaa Xaa Xaa Phe Xaa Xaa Cys
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope sequence
<220> FEATURE:
<221> NAME/KEY: MOD_RES
<222> LOCATION: (1)..(1)
<223> OTHER INFORMATION: Ser, Thr, Cys or not present
<220> FEATURE:
<221> NAME/KEY: MOD_RES
<222> LOCATION: (3)..(3)
<223> OTHER INFORMATION: Gln, Thr or Met
<220> FEATURE:
<221> NAME/KEY: MOD_RES
<222> LOCATION: (4)..(4)
<223> OTHER INFORMATION: Lys or Arg
<220> FEATURE:
<221> NAME/KEY: MOD_RES
<222> LOCATION: (5)..(5)
<223> OTHER INFORMATION: Leu or Met
<220> FEATURE:
<221> NAME/KEY: MOD_RES
<222> LOCATION: (6)..(6)
<223> OTHER INFORMATION: Trp, Tyr, Phe or Ile
<220> FEATURE:
<221> NAME/KEY: MOD_RES
<222> LOCATION: (8)..(8)
<223> OTHER INFORMATION: Asn, Glu, Ala or Cys
<220> FEATURE:
<221> NAME/KEY: MOD_RES
<222> LOCATION: (9)..(9)
```

<223> OTHER INFORMATION: May or may not be present

<400> SEQUENCE: 56

Xaa His Xaa Xaa Xaa Xaa Phe Xaa Cys
1               5

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: Synthetic
      amyloid-beta-peptide fragment sequence

<400> SEQUENCE: 57

His Gln Lys Leu Val Phe
1               5

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      amyloid-beta-peptide fragment sequence

<400> SEQUENCE: 58

His Gln Lys Leu Val Phe Phe Ala Glu Asp
1               5                   10

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 59

Ser His Thr Arg Leu Tyr Phe Cys
1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 60

His Met Arg Leu Phe Phe Asn Cys
1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (8)..(8)
<223> OTHER INFORMATION: May or may not be present

<400> SEQUENCE: 61

Ser His Gln Arg Leu Trp Phe Cys
1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 62

His Gln Lys Met Ile Phe Ala Cys
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 63

His Met Arg Met Tyr Phe Glu Cys
1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 64

Thr His Gln Arg Leu Trp Phe Cys
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: May or may not be present

<400> SEQUENCE: 65

His Gln Lys Met Ile Phe Cys
1               5
```

```
<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 66

Ser Gly Glu Tyr Val Phe His Cys
1               5

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 67

Ser Gly Gln Leu Lys Phe Pro Cys
1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 68

Ser Gly Gln Ile Trp Phe Arg Cys
1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 69

Ser Gly Glu Ile His Phe Asn Cys
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<221> NAME/KEY: MOD_RES
<222> LOCATION: (7)..(7)
<223> OTHER INFORMATION: May or may not be present

<400> SEQUENCE: 70

Gly Glu Leu Trp Phe Pro Cys
1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 71

Gly Glu Ile Trp Phe Glu Gly Cys
1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 72

Gly Glu Ile Tyr Phe Glu Arg Cys
1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 73

Gly Glu Ile Arg Phe Gly Ser Cys
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 74
```

```
Gly Glu Ile Lys Phe Asp His Cys
1               5
```

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 75

```
Gly Glu Ile Gln Phe Gly Ala Cys
1               5
```

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 76

```
Gly Gln Ile Trp Phe Ile Ser Cys
1               5
```

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 77

```
Gly Gln Ile Ile Phe Gln Ser Cys
1               5
```

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 78

```
Gly Gln Ile Arg Phe Asp His Cys
1               5
```

<210> SEQ ID NO 79
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 79

Gly Glu Met Trp Phe Ala Leu Cys
1               5

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 80

Gly Glu Leu Gln Phe Pro Pro Cys
1               5

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 81

Gly Glu Met Gln Phe Phe Ile Cys
1               5

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 82

Gly Glu Leu Tyr Phe Arg Ala Cys
1               5

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present
```

```
<400> SEQUENCE: 83

Gly Glu Ile Arg Phe Ala Leu Cys
1               5

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 84

Gly Met Ile Val Phe Pro His Cys
1               5

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 85

Gly Asp Leu Lys Phe Pro Leu Cys
1               5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 86

Gly Gln Ile Leu Phe Pro Val Cys
1               5

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 87

Gly Glu Leu Phe Phe Pro Lys Cys
1               5

<210> SEQ ID NO 88
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 88

Gly Gln Ile Met Phe Pro Arg Cys
1               5

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 89

Gly Ser Leu Phe Phe Trp Pro Cys
1               5

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 90

Gly Glu Ile Leu Phe Gly Met Cys
1               5

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 91

Gly Gln Leu Lys Phe Pro Phe Cys
1               5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
```

<223> OTHER INFORMATION: May or may not be present

<400> SEQUENCE: 92

Gly Thr Ile Phe Phe Arg Asp Cys
1               5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 93

Gly Gln Ile Lys Phe Ala Gln Cys
1               5

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 94

Gly Thr Leu Ile Phe His His Cys
1               5

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 95

Gly Gln Ile Gln Phe Pro Leu Cys
1               5

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 96

Gly Glu Leu Phe Phe Glu Lys Cys
1               5

```
<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 97

Gly Glu Ile Arg Phe Glu Leu Cys
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: May or may not be present

<400> SEQUENCE: 98

Ser Gly Glu Ile Tyr Phe Glu Arg Cys
1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: May or may not be present

<400> SEQUENCE: 99

Ala Gly Glu Ile Tyr Phe Glu Arg Cys
1               5

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present

<400> SEQUENCE: 100

Cys Gly Glu Ile Tyr Phe Glu Arg
1               5

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (8)..(8)
<223> OTHER INFORMATION: May or may not be present

<400> SEQUENCE: 101

Ala Ile Pro Leu Phe Val Met Cys
1               5

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 102

Lys Leu Pro Leu Phe Val Met Cys
1               5

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 103

Gln Leu Pro Leu Phe Val Leu Cys
1               5

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: May or may not be present

<400> SEQUENCE: 104

Asn Asp Ala Lys Ile Val Phe Cys
1               5

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: May or may not be present

<400> SEQUENCE: 105
```

```
Gly Glu Ile Tyr Phe Glu Arg Cys
1               5
```

<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 106

```
His His His His His His
1               5
```

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

```
Ser His Thr Arg Leu Tyr Phe
1               5
```

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

```
Ser Gly Glu Tyr Val Phe His
1               5
```

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

```
Ser Gly Gln Leu Lys Phe Pro
1               5
```

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

```
Ser Gly Gln Ile Trp Phe Arg
1               5
```

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic

```
                              peptide

<400> SEQUENCE: 111

Ser Gly Glu Ile His Phe Asn
1               5

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Gln Ile Trp Phe Ile Ser
1               5

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Asn Asp Ala Lys Ile Val Phe
1               5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gly Gln Ile Ile Phe Gln Ser
1               5

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Gln Ile Arg Phe Asp His
1               5

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

His Met Arg Leu Phe Phe Asn
1               5

<210> SEQ ID NO 117
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gly Glu Met Trp Phe Ala Leu
1               5

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly Glu Leu Gln Phe Pro Pro
1               5

<210> SEQ ID NO 119
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gly Glu Leu Trp Phe Pro
1               5

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ser His Gln Arg Leu Trp Phe
1               5

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

His Gln Lys Met Ile Phe Ala
1               5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gly Glu Met Gln Phe Phe Ile
1               5
```

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gly Glu Leu Tyr Phe Arg Ala
1               5

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gly Glu Ile Arg Phe Ala Leu
1               5

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gly Met Ile Val Phe Pro His
1               5

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Glu Ile Trp Phe Glu Gly
1               5

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gly Glu Ile Tyr Phe Glu Arg
1               5

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 128

Ala Ile Pro Leu Phe Val Met
1               5

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gly Asp Leu Lys Phe Pro Leu
1               5

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Gln Ile Leu Phe Pro Val
1               5

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gly Glu Leu Phe Phe Pro Lys
1               5

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gly Gln Ile Met Phe Pro Arg
1               5

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

His Met Arg Met Tyr Phe Glu
1               5

<210> SEQ ID NO 134
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 134

Gly Ser Leu Phe Phe Trp Pro
1               5

<210> SEQ ID NO 135
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gly Glu Ile Leu Phe Gly Met
1               5

<210> SEQ ID NO 136
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gly Gln Leu Lys Phe Pro Phe
1               5

<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Lys Leu Pro Leu Phe Val Met
1               5

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gly Thr Ile Phe Phe Arg Asp
1               5

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Thr His Gln Arg Leu Trp Phe
1               5
```

<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gly Gln Ile Lys Phe Ala Gln
1               5

<210> SEQ ID NO 141
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Thr Leu Ile Phe His His
1               5

<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gly Glu Ile Arg Phe Gly Ser
1               5

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Gln Ile Gln Phe Pro Leu
1               5

<210> SEQ ID NO 144
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Glu Ile Lys Phe Asp His
1               5

<210> SEQ ID NO 145
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

```
-continued

Gly Glu Ile Gln Phe Gly Ala
1               5

<210> SEQ ID NO 146
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gln Leu Pro Leu Phe Val Leu
1               5

<210> SEQ ID NO 147
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

His Gln Lys Met Ile Phe
1               5

<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Glu Leu Phe Phe Glu Lys
1               5

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Glu Ile Arg Phe Glu Leu
1               5

<210> SEQ ID NO 150
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ser Gly Glu Ile Tyr Phe Glu Arg
1               5

<210> SEQ ID NO 151
<211> LENGTH: 8
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 151

Ala Gly Glu Ile Tyr Phe Glu Arg
1               5

<210> SEQ ID NO 152
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Glu Val His His Gln Lys Leu Val Phe Phe Ala Glu Asp
1               5                  10

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyroglutamate

<400> SEQUENCE: 153

Glu Val His His Gln Lys Leu Val Phe
1               5

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

His Gln Lys Leu Val Phe Cys
1               5

COMPOUNDS FOR TREATING AMYLOIDOSES

This application is a National Stage of PCT/AT09/000,235 filed Jun. 12, 2009 and claims the benefit of Austrian patent application A 952/2008 filed Jun. 12, 2008.

SEQUENCE LISTING

The instant application contains a Sequence Listing which has been submitted in ASCII format via EFS-Web and is hereby incorporated by reference in its entirety. Said ASCII copy, created on Feb. 3, 2012, is named 372886US.txt and is 39,750 bytes in size.

The present invention relates to the prevention, treatment and diagnosis of diseases associated with β-amyloid formation and/or aggregation (β-Amyloidoses). More particularly, the present invention provides new mimotopes eliciting an immune response directed against β-amyloid and N-terminally truncated and/or posttranslationally modified β-amyloid fragments and new antibodies recognizing said mimotopes and Aβ peptides for use in the prevention, treatment and diagnosis of diseases associated with β-amyloid formation and/or aggregation.

Various degenerative diseases are characterized by the aberrant polymerization and accumulation of specific proteins so called proteopathies. The present invention relates to the prevention, treatment and diagnosis of proteopathies associated with β-amyloid proteins summarised under the term β-Amyloidoses. The most prominent form of β-Amyloidoses is Alzheimer's disease (AD). Other examples include but are not limited to Dementia with Lewy bodies and Dementia in Down syndrome.

AD is the most common form of dementia in humans. So far no effective treatment is available to stop the progressive neurodegeneration and associated cognitive decline in human patients. AD is characterized by the abnormal accumulation of extracellular amyloid plaques—closely associated with extensive astrocytosis and microgliosis as well as dystrophic neurones and neuronal loss. These amyloid plaques mainly consist of the Amyloid-β (Aβ; derived from APP (gi:112927) peptides Aβ40 and Aβ42 derived from the Amyloid Precursor Protein (APP), which is expressed on various cell types in the nervous system. Aβ peptides are considered to be directly involved in the pathogenesis and progression of AD. Consequently, reduction of Aβ burden in the brain is predicted to slow down or halt disease progression and could also stop cognitive decline in AD patients.

APP is normally processed by two cleavage steps to form the currently known forms of Abeta x-40/42/43. The first cleavage is performed by the so called beta-site APP-cleaving enzymes 1 and 2 (BACE1 and BACE2); the second proteolytic step is performed by the gamma-Secretase Complex.

BACE enzymes recognise two sites in the N-terminal portion of the presumptive Aβ peptide and proteolytic activity of BACE leads to the formation of Abeta 1-X and 11-X respectively. Thus BACE mediated APP processing creates a variety of different Aβ species with full length Abeta 1-40/42 as major contribuent. Gamma-Secretase activity leads to production of 3 main fragments: Aβ 1-40/42/43. Once these peptides are produced they are further processed by Aminopeptidases resulting in their subsequent stepwise degradation. These further steps lead to formation of other forms like for example Aβ3-40/42 respectively.

The third family of proteolytic enzymes involved in APP processing is the so called alpha-Secretase family (ADAM ('a disintegrin and metalloprotease') family). Alpha secretases cleave amyloid precursor protein (APP) in its transmembrane region (between aa16 and aa17 of the Aβ peptide sequence) and preclude the formation of Aβ peptides. Thus alpha Secretase cleavage is the crucial step for non-amyloidogenic APP processing. Specifically, alpha secretases cleavage results in release of a secreted form called sAPPalpha. sAPPalpha is considered to be sufficient to mediate most of physiological functions of APP and may serve as a signalling molecule. Evidence suggests that the shed ectodomain plays a role in the growth of fibroblasts in culture. sAPP was found to be neuroprotective for primary neurons in culture, preventing elevations in intracellular Ca2+ levels caused by glucose deprivation and raising the excitotoxic threshold of glutamate, as well as mediating axonal and dendritic growth.

In humans on average 60-85% of amyloid plaque material is formed by Aβ40/42 derivatives which are N-terminally truncated and frequently modified. The relative amounts of N-terminally truncated Aβ species are variable in respect of Aβ levels, mutations and BACE activity. The most abundant truncated forms of Aβ are: Aβ3-40/42 and Aβ11-40/42 thought to constitute up to 50% of all truncated forms. This means that these isoforms constitute 25-40% of all amyloid peptides in AD brains. Both peptides contain an N-terminal glutamate residue, which is frequently modified enzymatically to pyro-glutamate, resulting in the formation of Aβ3 (pE)-40/42 and Aβ11(pE)-40/42, respectively. Because the amino terminus of the Abeta 3(pE) and 11(pE) peptides is blocked by internal lactam, it is protected from the proteolytic action of aminopeptidases other than pyroglutamate-specific ones and can thus remain stable in tissues. Additional N-terminally truncated amyloid variants starting at position 2, 3, 4, 5, 6, 7, 8, 9, or 10 of beta amyloid can be detected in AD patients. These forms are frequently post translationally modified, e.g. by methylation.

It has been shown previously that truncated and modified peptides are more stable in neural tissue than full length Aβ. Additionally, N-terminally truncated forms of Aβ are more amyloidogenic than unmodified Aβ peptides, thus enhancing the rate of plaque formation, and also show neurotoxic activity when applied to neurons in culture as well as in in vivo experiments. Truncated forms of Aβ can already be detected in diffuse aggregations of Aβ in early stages of AD and might be involved in early plaque formation, acting as individual seeds in vivo. Due to these effects it is suggested that Aβ x-40/42 peptides may initiate and/or accelerate plaque formation, perhaps by acting as nucleating centers that seed the subsequent deposition of relatively less amyloidogenic but apparently more abundant full-length Aβ peptides. Furthermore, there is compelling evidence that the occurrence of N-terminally truncated Aβ species is correlated with increasing severity and early onset of neurodegeneration in sporadic and familial Alzheimer disease as well as Down Syndrome patients. Data from such patients are implying a link between early formation of truncated Aβ species and disease onset as well as progression. In summary, the findings predict that N-terminal heterogeneity of Aβ peptides, demonstrated to occur both in vitro and in AD brain, may accelerate Aβ deposition into plaques. Thus, proteolytic events contributing to the cleavage of APP within the N-terminal domain of Aβ may be of considerable significance in the pathogenesis of AD and related disorders.

In light of these findings it seems to be important to decrease the amount of these peptide species in AD patients to modify disease progression and reduce toxicity and accompanying cognitive decline. An optimal AD-vaccine should thus elicit an immune response which is able to target the most prominent forms of Aβ peptides present in the brain of AD patients, Aβ1-40/42, Aβ3-40/42 as well as Aβ3(p) E-40/42 and Aβ11-40/42 as well as Aβ11(p) E-40/42 without interfering with physiological functions of APP signalling, notably the functions of sAPPalpha.

Immunotherapeutic treatment using active and passive immunisation strategies to target full length Aβ, led to reduction of Aβ plaques and had beneficial impact on disease progression in animal models of AD. All of the active vaccination approaches tested in mouse models used full length Aβ40/42 or fragments containing the native sequence of Aβ.

However, the first phase IIa clinical vaccination trial in AD patients using full length Aβ42 as antigen had to be discontinued due to severe neuroinflammatory side effects including brain infiltration of autoreactive T-cells (Nicoll, J. A. et al. 2003 Nat Med 9:448-452; Bayer, A. J., et al. 2005 Neurology 64:94-101). Nevertheless, studies investigating the clinical effects in patients treated with AN-1792 revealed that patients who developed an antibody response against Aβ42 but did not suffer from meningoencephalitis performed better in cognitive tests than non-responding patients, indicating that immunotherapy might be a useful treatment approach in AD.

Most importantly, recent results obtained from autopsy cases analysing patients which underwent AN1792 vaccination showed a clearance of full length Aβ species from the brain but a persistence of N-terminally truncated forms of Aβ (Nicoll, J. A., et, al. 2006 J Neuropathol Exp Neurol 65:1040-1048). This underscores the necessity of the invention of novel vaccines which are targeting full length Aβ as well as N-terminally truncated and modified forms of this molecule.

Inducing an immune response against Aβ40/42 peptides in humans can interfere with cognitive decline in AD patients, but a safe Alzheimer vaccine has to avoid the formation of autoreactive T cells. Vaccination using native Aβ40/42 peptides or fragments thereof suffers from the intrinsic risk of inducing autoimmune disease in patients, as the immune response can not exclusively be targeted to Aβ.

It is an object of the present invention to provide compounds and medicaments which can be used to treat and/or prevent Alzheimer's disease. These compounds should show no or a significantly reduced risk of inducing autoimmune diseases when administered to an individual. According to another object of the present invention said compound may be able to induce the in vivo formation of antibodies in an individual which are directed to truncated and/or stabilised forms of Aβ, which usually are major components of amyloid deposits.

Therefore the present invention relates to the use of at least one compound comprising the amino acid sequence $(X_1)_m HX_2 X_3 X_4 X_5 FX_6 (X_7)_n$   (Formula II) (SEQ ID NO: 56), wherein
$X_1$ is serine (S), threonine (T) or cysteine (C),
$X_2$ is glutamine (Q), threonine (T) or methionine (M),
$X_3$ is lysine (K) or arginine (R),
$X_4$ is leucine (L), methionine (M),
$X_5$ is tryptophane (W), tyrosine (Y), phenylalanine (F) or isoleucine (I),
$X_6$ is asparagine (N), glutamic acid (E), alanine (A) or cysteine (C),
$X_7$ is cysteine (C),
n and m are, independently, 0 or 1,
said compound having a binding capacity to an antibody which is specific for an epitope of the amyloid-beta-peptide (Aβ) comprising the amino acid sequence HQKLVF (SEQ ID NO: 57) and/or HQKLVFFAED (SEQ ID NO: 58).

for producing a medicament for preventing and/or treating Alzheimer's disease.

The invention presented herein refers to antigens which do not contain sequences of the native Aβ peptide but are however mimicking the structure of neo-epitopes of Aβ not detectable by Mimotopes such as described in the WO 2004/062556. Such a Mimotope-based AD vaccine therefore induces antibody responses exclusively reacting with the pathological Aβ molecules mentioned above but not with parental structures. Importantly, the immune response induced by these Mimotopes does not interact with full length APP and secreted APPalpha (sAPPalpha) and thus the vaccination retains normal physiologic functions of both molecules. Furthermore, Mimotopes do not contain potential T-cell self-epitopes and avoid induction of detrimental autoreactive T-cells.

It surprisingly turned out, that a compound comprising an amino acid sequence of the formula I is able to induce the in vivo formation of antibodies which are directed to the non truncated Aβ form Aβ1-40/42, and N-terminally truncated forms like Aβ3-40/42, Aβ(pE)3-40/42, unmodified Aβ11-40/42, modified Aβp (E)11-40/42 and Aβ14-40/42, respectively, and also to further N-terminally truncated and posttranslationally modified amyloid variants starting at position 2, 4, 5, 6, 7, 8, 9, or 10 of Aβ. Importantly, these mimotopes do not induce a cross reactivity to the neoepitopes present in sAPP alpha after cleavage from APP and thus do not interfere with normal sAPP alpha signalling.

The antibodies formed by the vaccination of the molecules (mimotopes) of the present invention are able to bind to the Aβ fragments listed above resulting in the disintegration of Aβ plaques.

Formula I and II and all other peptidic molecules disclosed herein mimic the natural occurring Aβ peptides and variants Aβ1-40/42, AβpE3-40/42, Aβ3-40/42 and Aβ11-40/42, AβpE11-40/42 and Aβ14-40/42 so that compounds comprising the amino acid sequences disclosed herein are able to induce the formation of respective antibodies. Additional N-terminally truncated and posttranslationally modified amyloid variants starting at position 2, 4, 5, 6, 7, 8, 9, or 10 of Aβ can be detected by such anti-bodies as well.

"β-Amyloidoses", as used herein, refers to various degenerative diseases which are characterized by the aberrant polymerization and accumulation of specific proteins so called proteopathies. The present invention relates to the prevention, treatment and diagnosis of proteopathies associated with β-amyloid proteins summarized under the term β-Amyloidoses. The most prominent form of β-Amyloidoses is Alzheimer's disease (AD). Other examples include but are not limited to Dementia with Lewy bodies and Dementia in Down syndrome. Further examples are Lewy body dementia, myositis, sporadic inclusion body myositis, hereditary cerebral hemorrhage with amyloidosis (Dutch type), cerebral amyloid angiopathy, Aβ related angiitis.

The administration of a compound comprising an amino acid sequence of formula II provokes an immune response against the same non-truncated and truncated and post translationally modified forms of Aβ as the compounds comprising an amino acid sequence of formula I.

According to a preferred embodiment of the present invention the compound comprises a peptide having an amino acid sequence selected from the group consisting of SHTRLYF(C) (SEQ ID NO: 59), HMRLFFN(C) (SEQ ID NO: 60), SHQRLWF(C) (SEQ ID NO: 61), HQKMIFA(C) (SEQ ID NO: 62), HMRMYFE(C) (SEQ ID NO: 63), THQRLWF(C) (SEQ ID NO: 64) and HQKMIF(C) (SEQ ID NO: 65), preferably from the group consisting of SHTRLYF(C) (SEQ ID NO: 59), HMRLFFN(C) (SEQ ID NO: 60), HQKMIFA(C) (SEQ ID NO: 62), HMRMYFE(C) (SEQ ID NO: 63), THQRLWF(C)

(SEQ ID NO: 64) (all of which are able to induce in vivo the formation of antibodies directed to Aβ peptides).

According to a further preferred embodiment of the present invention the at least one compound comprises a peptide having amino acid sequence SHTRLYF(C) (SEQ ID NO: 59), SGEYVFH(C) (SEQ ID NO: 66), SGQLKFP(C) (SEQ ID NO: 67), SGQIWFR(C) (SEQ ID NO: 68), SGEIHFN(C) (SEQ ID NO: 69), HMRLFFN(C) (SEQ ID NO: 60), GELWFP(C) (SEQ ID NO: 70), HQKMIFA(C) (SEQ ID NO: 62), GEIWFEG(C) (SEQ ID NO: 71), GEIYFER(C) (SEQ ID NO: 72), THQRLWF(C) (SEQ ID NO: 64), GEIRFGS(C) (SEQ ID NO: 73), GEIKFDH(C) (SEQ ID NO: 74) or GEIQFGA(C) (SEQ ID NO: 75), in particular HQKMIFA(C) (SEQ ID NO: 62).

Another aspect of the present invention relates to the use of at least one compound comprising the amino acid sequence $$(X_1)_m GX_2X_3X_4FX_5X_6(X_7)_n \quad \text{(Formula I) (SEQ ID NO: 55),}$$

wherein
- $X_1$ is serine (S), alanine (A) or cysteine (c),
- $X_2$ is serine (S), threonine (T), glutamic acid (E), aspartic acid (D), glutamine (Q) or methionine (M),
- $X_3$ is isoleucine (I), tyrosine (Y), methionine (M) or leucine (L),
- $X_4$ is leucine (L), arginine (R), glutamine (Q), tryptophan (W), valine (V), histidine (H), tyrosine (Y), isoleucine (I), lysine (K) methionine (M) or phenylalanine (F),
- $X_5$ is alanine (A), phenylalanine (F), histidine (H), asparagine (N), arginine (R), glutamic acid (E), isoleucine (I), glutamine (Q), aspartic acid (D), proline (P) or tryptophane (W), glycine (G),
- $X_6$ is any amino acid residue,
- $X_7$ is cysteine (C),
- m and n are, independently, 0 or 1, said compound having a binding capacity to an antibody which is specific for an epitope of the amyloid-beta-peptide (Aβ) comprising the amino acid sequence HQKLVF (SEQ ID NO: 57) and/or HQKLVFFAED (SEQ ID NO: 58).

for producing a medicament for preventing and/or treating Alzheimer's disease.

According to a preferred embodiment of the present invention the compound comprises a peptide having an amino acid sequence selected from the group consisting of SGEYVFH(C) (SEQ ID NO: 66), SGQLKFP(C) (SEQ ID NO: 67), SGQIWFR(C) (SEQ ID NO: 68), SGEIHFN(C) (SEQ ID NO: 69), GQIWFIS(C) (SEQ ID NO: 76), GQIIFQS(C) (SEQ ID NO: 77), GQIRFDH(C) (SEQ ID NO: 78), GEMWFAL(C) (SEQ ID NO: 79), GELQFPP(C) (SEQ ID NO: 80), GELWFP(C) (SEQ ID NO: 70), GEMQFFI(C) (SEQ ID NO: 81), GELYFRA(C) (SEQ ID NO: 82), GEIRFAL(C) (SEQ ID NO: 83), GMIVFPH(C) (SEQ ID NO: 84), GEIWFEG(C) (SEQ ID NO: 71), GDLKFPL(C) (SEQ ID NO: 85), GQILFPV(C) (SEQ ID NO: 86), GELFFPK(C) (SEQ ID NO: 87), GQIMFPR(C) (SEQ ID NO: 88), GSLFFWP(C) (SEQ ID NO: 89), GEILFGM(C) (SEQ ID NO: 90), GQLKFPF(C) (SEQ ID NO: 91), GTIFFRD(C) (SEQ ID NO: 92), GQIKFAQ(C) (SEQ ID NO: 93), GTLIFHH(C) (SEQ ID NO: 94), GEIRFGS(C) (SEQ ID NO: 73), GQIQFPL(C) (SEQ ID NO: 95), GEIKFDH(C) (SEQ ID NO: 74), GEIQFGA(C) (SEQ ID NO: 75), GELFFEK(C) (SEQ ID NO: 96), GEIRFEL(C) (SEQ ID NO: 97), GEIYFER(C) (SEQ ID NO: 72), SGEIYFER(C) (SEQ ID NO: 98), AGEIYFER(C) (SEQ ID NO: 99) and (C)GEIYFER (SEQ ID NO: 100).

Particularly preferred compounds of the present invention comprise or consist of the above identified amino acid sequences, whereby the C-terminus of said peptide may or may not comprise a cysteine residue (indicated by the use of brackets) so that the compound obtained may be coupled, e.g., to a carrier molecule. However, it is of course also possible to link to the N-terminus of said peptide a cysteine residue.

According to a particularly preferred embodiment of the present invention the amino acid sequence is selected from the group consisting of GELWFP(C) (SEQ ID NO: 70), GEIWFEG(C) (SEQ ID NO: 71), GEIYFER(C) (SEQ ID NO: 72), GEILFGM(C) (SEQ ID NO: 90), GEIKFDH(C) (SEQ ID NO: 74), GEIQFGA(C) (SEQ ID NO: 75) (all of which are competing peptides) and GEIKFDH(C) (SEQ ID NO: 74), GEIRFGS(C) (SEQ ID NO: 73), SGQLKFP(C) (SEQ ID NO: 67), SGQIWFR(C) (SEQ ID NO: 68), SGEIHFN(C) (SEQ ID NO: 69), GELWFP(C) (SEQ ID NO: 70), GEIWFEG(C) (SEQ ID NO: 71), GEIYFER(C) (SEQ ID NO: 72), GEIQFGA(C) (SEQ ID NO: 75), SGEYVFH(C) (SEQ ID NO: 66) (all of which are able to induce in vivo the formation of antibodies directed to Aβ peptides listed above).

Another aspect of the present invention relates to the use of at least one compound comprising an amino acid sequence selected from the group consisting of AIPLFVM(C) (SEQ ID NO: 101), KLPLFVM(C) (SEQ ID NO: 102), QLPLFVL(C) (SEQ ID NO: 103) and NDAKIVF(C) (SEQ ID NO: 104) for producing a medicament for preventing and/or treating Alzheimer's disease.

Each of the compounds of the present invention is able to induce the in vivo formation of antibodies directed to peptides derived from Aβ40/42 including Aβ1-40/42, and N-terminally truncated forms like Aβ3-40/42, Aβ(pE)3-40/42, unmodified Aβ11-40/42, modified Aβp(E)11-40/42 and Aβ14-40/42, respectively. Since the compounds of the present invention are isolated by an antibody which is directed to amino acid residues 14 to 19 of Aβ, the compounds of the present invention are able to induce the formation of antibodies which can bind to truncations of the Aβ peptide starting from amino acid position 2, 3, 4, 5, 6, 7, 8, 9, 10, 11, 12, 13 or 14 of the Aβ peptides. Therefore these compounds are particularly well suited to treat and/or prevent AD because the administration of at least one of said compounds results in the formation of antibodies which are capable to recognize the major Aβ forms, e.g. Aβ1-40/42, AβpE3-40/42 and Aβ3-40/42. These mimotopes furthermore fail to induce a cross reactivity to the neoepitopes present in sAPP alpha after cleavage from APP and thus do not interfere with normal sAPP alpha signalling.

The compounds of the present invention, in particular the peptides of the present invention may further be modified at their N-terminus by an acylation and/or acetylation reaction. For instance, a particularly preferred compound comprises the amino acid sequence AC-GEIYFER(C) (SEQ ID NO: 105).

According to the present invention the term "mimotope" refers to a molecule which has a conformation that has a topology equivalent to the epitope of which it is a mimic. The mimotope binds to the same antigen-binding region of an antibody which binds immunospecifically to a desired antigen. The mimotope will elicit an immunological response in a host that is reactive to the antigen to which it is a mimic. The mimotope may also act as a competitor for the epitope of which it is a mimic in in vitro inhibition assays (e.g. ELISA inhibition assays) which involve the epitope and an antibody binding to said epitope. However, a mimotope of the present invention may not necessarily prevent or compete with the binding of the epitope of which it is a mimic in an in vitro inhibition assay although it is capable to induce a specific immune response when administered to a mammal.

As used herein, the term "epitope" refers to an immunogenic region of an antigen which is recognized by a particular anti-body molecule. In general, an antigen will possess one or more epitopes, each capable of binding an antibody that recognizes the particular epitope.

The mimotopes of the present invention can be synthetically produced by chemical synthesis methods which are well known in the art, either as an isolated peptide or as a part of another peptide or polypeptide. Alternatively, the peptide mimotope can be produced in a microorganism which produces the peptide mimotope which is then isolated and if desired, further purified. The peptide mimotope can be produced in microorganisms such as bacteria, yeast or fungi, in eukaryote cells such as a mammalian or an insect cell, or in a recombinant virus vector such as adenovirus, poxvirus, herpesvirus, Simliki forest virus, baculovirus, bacteriophage, sindbis virus or sendai virus. Suitable bacteria for producing the peptide mimotope include *E. coli, B. subtilis* or any other bacterium that is capable of expressing peptides such as the peptide mimotope. Suitable yeast types for expressing the peptide mimotope include *Saccharomyces cerevisiae, Schizosaccharomyces pombe, Candida, Pichia pastoris* or any other yeast capable of expressing peptides. Corresponding methods are well known in the art. Also methods for isolating and purifying recombinantly produced peptides are well known in the art and include e.g. as gel filtration, affinity chromatography, ion exchange chromatography etc.

To facilitate isolation of the peptide mimotope, a fusion polypeptide may be made wherein the peptide mimotope is translationally fused (covalently linked) to a heterologous polypeptide which enables isolation by affinity chromatography. Typical heterologous polypeptides are His-Tag (e.g. $His_6$; 6 histidine residues (SEQ ID NO: 106)), GST-Tag (Glutathione-S-transferase) etc. The fusion polypeptide facilitates not only the purification of the mimotopes but can also prevent the mimotope polypeptide from being degraded during purification. If it is desired to remove the heterologous polypeptide after purification the fusion polypeptide may comprise a cleavage site at the junction between the peptide mimotope and the heterologous polypeptide. The cleavage site consists of an amino acid sequence that is cleaved with an enzyme specific for the amino acid sequence at the site (e.g. proteases).

The mimotopes of the present invention may also be modified at or nearby their N- and/or C-termini so that at said positions a cysteine residue is bound thereto. In a preferred embodiment terminally positioned (located at the N- and C-termini of the peptide) cysteine residues are used to cyclize the peptides through a disulfide bond.

The mimotopes of the present invention may also be used in various assays and kits, in particular in immunological assays and kits. Therefore, it is particularly preferred that the mimotope may be part of another peptide or polypeptide, particularly an enzyme which is used as a reporter in immunological assays. Such reporter enzymes include e.g. alkaline phosphatase or horseradish peroxidase.

The mimotopes according to the present invention preferably are antigenic polypeptides which in their amino acid sequence vary from the amino acid sequence of Aβ or of fragments of Aβ. In this respect, the inventive mimotopes may not only comprise amino acid substitutions of one or more naturally occurring amino acid residues but also of one or more non-natural amino acids (i.e. not from the 20 "classical" amino acids) or they may be completely assembled of such non-natural amino acids. Moreover, the inventive antigens which induce antibodies directed and binding to Aβ1-40/42, AβpE3-40/42, Aβ3-40/42, Aβ11-40/42, AβpE11-40/42 and Aβ14-40/42 (and other N-terminally truncated forms of β starting from amino acid positions 2, 3, 4, 5, 6, 7, 8, 9, 10, 11, 12 and 13) may be assembled of D- or L-amino acids or of combinations of DL-amino acids and, optionally, they may have been changed by further modifications, ring closures or derivatizations. Suitable antibody-inducing antigens may be provided from commercially available peptide libraries. Preferably, these peptides are at least 7 amino acids, and preferred lengths may be up to 16, preferably up to 14 or 20 amino acids (e.g. 5 to 16 amino acid residues). According to the invention, however, also longer peptides may very well be employed as antibody-inducing antigens. Furthermore the mimotopes of the present invention may also be part of a polypeptide and consequently comprising at their N- and/or C-terminus at least one further amino acid residue.

For preparing the mimotopes of the present invention (i.e. the antibody-inducing antigens disclosed herein), of course also phage libraries, peptide libraries are suitable, for instance produced by means of combinatorial chemistry or obtained by means of high throughput screening techniques for the most varying structures (Display: A Laboratory Manual by Carlos F. Barbas (Editor), et al.; Willats W G Phage display: practicalities and prospects. Plant Mol. Biol. 2002 December; 50(6):837-54).

Furthermore, according to the invention also anti-Aβ1-40/42-, -AβpE3-40/42-, -Aβ3-40/42-, -Aβ11-40/42- AβpE11-40/42- and Aβ14-40/42-antibody-inducing antigens based on nucleic acids ("aptamers") may be employed, and these, too, may be found with the most varying (oligonucleotide) libraries (e.g. with 2-180 nucleic acid residues) (e.g. Burgstaller et al., Curr. Opin. Drug Discov. Dev. 5(5) (2002), 690-700; Famulok et al., Acc. Chem. Res. 33 (2000), 591-599; Mayer et al., PNAS 98 (2001), 4961-4965, etc.). In antibody-inducing antigens based on nucleic acids, the nucleic acid backbone can be provided e.g. by the natural phosphor-diester compounds, or also by phosphorothioates or combinations or chemical variations (e.g. as PNA), wherein as bases, according to the invention primarily U, T, A, C, G, H and mC can be employed. The 2'-residues of the nucleotides which can be used according to the present invention preferably are H, OH, F, Cl, $NH_2$, O-methyl, O-ethyl, O-propyl or O-butyl, wherein the nucleic acids may also be differently modified, i.e. for instance with protective groups, as they are commonly employed in oligonucleotide synthesis. Thus, aptamer-based antibody-inducing antigens are also preferred antibody-inducing antigens within the scope of the present invention.

According to a preferred embodiment of the present invention the compound is coupled to a pharmaceutically acceptable carrier, preferably KLH (Keyhole Limpet Hemocyanin), tetanus toxoid, albumin-binding protein, bovine serum albumin, a dendrimer (MAP; Biol. Chem. 358: 581), peptide linkers (or flanking regions) as well as the adjuvant substances described in Singh et al., Nat. Biotech. 17 (1999), 1075-1081 (in particular those in Table 1 of that document), and O'Hagan et al., Nature Reviews, Drug Discovery 2 (9) (2003), 727-735 (in particular the endogenous immuno-potentiating compounds and delivery systems described therein), or mixtures thereof. The conjugation chemistry (e.g. via heterobifunctional compounds such as GMBS and of course also others as described in "Bioconjugate Techniques", Greg T. Hermanson) in this context can be selected from reactions known to the skilled man in the art. Moreover, the vaccine composition may be formulated with an adjuvant, preferably a low soluble aluminium composition, in particular aluminium hydroxide. Of course, also adjuvants like MF59 aluminium phosphate, calcium phosphate, cytokines (e.g., IL-2, IL-12, GM-CSF), saponins (e.g., QS21), MDP derivatives, CpG oligos, LPS, MPL, polyphosphazenes, emulsions (e.g., Freund's, SAF), liposomes, virosomes, iscoms, cochleates, PLG microparticles, poloxamer particles, virus-like particles, heat-labile enterotoxin (LT), cholera toxin (CT), mutant toxins (e.g., LTK63 and LTR72), microparticles and/or polymerized liposomes may be used.

The compound of the present invention is preferably bound to the carrier or adjuvant via a linker, which is selected from the group consisting of NHS-poly (ethylene oxide) (PEO) (e.g. NHS-PEO$_4$-maleimide).

A vaccine which comprises the present compound (mimotope) and the pharmaceutically acceptable carrier may be administered by any suitable mode of application, e.g. i.d., i.v., i.p., i.m., intranasally, orally, subcutaneously, etc. and in any suitable delivery device (O'Hagan et al., Nature Reviews, Drug Discovery 2 (9), (2003), 727-735). The compound of the present invention is preferably formulated for intravenous, subcutaneous, intradermal or intramuscular administration (see e.g. "Handbook of Pharmaceutical Manufacturing Formulations", Sarfaraz Niazi, CRC Press Inc, 2004).

The medicament (vaccine) according to the present invention contains the compound according to the invention in an amount of from 0.1 ng to 10 mg, preferably 10 ng to 1 mg, in particular 100 ng to 100 µg, or, alternatively, e.g. 100 fmol to 10 µmol, preferably 10 pmol to 1 µmol, in particular 100 pmol to 100 nmol. Typically, the vaccine may also contain auxiliary substances, e.g. buffers, stabilizers etc.

Another aspect of the present invention relates to the use of a compound as defined above for treating and/or ameliorating symptoms of synucleopathy.

It surprisingly turned out that the compounds of the present invention can also be used to treat and ameliorate symptoms associated with synucleopathies.

Amyloidoses and synucleopathies are associated with the cerebral accumulation of β-amyloid and α-synuclein, respectively. Some patients show clinical and pathological features of both diseases, raising the possibility of overlapping pathogenic pathways. These patients are also classified as suffering from a newly identified syndrome described as Dementia with Lewy Bodies or Parkinson's disease with dementia (DLB/PDD). In a recent transgenic animal model for DLB/PDD it has been shown that overexpression of both, α-synuclein and Amyloid Precursor Protein (hAPP), in mice leads to the development of cognitive and motor alterations accompanied by loss of cholinergic neurons and reduction in synaptic vesicles, formation of extensive amyloid plaques, and haSYN-immunoreactive intraneuronal fibrillar inclusions. All of these features are also found in the DLB/PDD syndrome. It has been described recently that both molecules are potentially able to interact and to form hybrid oligomers in vitro. It has also been shown that overexpression of the APP can exacerbate some of the pathologic effects of α-synuclein overexpression. In contrast, α-synuclein is able to enhance secretion and toxicity of amyloid beta peptides and could thus also increase the effects of β-amyloid supporting the notion of overlapping pathogenic pathways in neurodegenerative processes.

In both proteopathies progressive accumulation of peptide oligomers has been identified as one of the central toxic events leading to the various alterations typical for either synucleopathies or amyloidoses. Despite this mechanistic similarity, it is hypothesized that α-synuclein and Aβ have distinct, as well as convergent, pathogenic effects on the integrity and function of the brain. Synucleins are believed to affect motoric function more severely than cognitive function, whereas amyloid β peptides are described to have opposite effects. The reason for this discrepancy is currently unknown but it precludes a clear description of the interdependencies and effects of both molecules.

The treatment approach presented in the current invention is describing an immunotherapy targeting Aβ which will lead to the removal of mainly extracellular amyloid. It is thus believed to relieve the amyloid associated alterations ranging from plaque deposition to neuronal death as well as to memory problems and cognitive decline. The subcellular localization of synucleins however indicates that these intracellular proteins are mainly active at the synapse, especially confined to synaptic vesicles. Interestingly, also synuclein accumulations, which are the unifying pathologic hallmark of synucleopathies, are mainly detectable intracellularly. Additionally, the pathogenic mechanism underlying synucleopathies is believed to be attributable to intraneuronal changes ranging from mitochondrial dysfunction, accumulation of abnormally folded, ubiquitinated or phosphorylated proteins as well as accumulation of alpha synuclein. These alterations are consequently resulting in changes in synaptic functions, synaptic failure, and loss of dopaminergic neurons and classical clinical signs of synucleopathies. In contrast Aβ is mainly detectable extraneuronally and amyloid plaques as well as fibrils, protofibrils and oligomers of beta amyloid can exert neurotoxic functions when applied extracellularly or intracerebrally. Thus it is a surprising finding to the expert that an approach mainly targeting extracellular amyloid would reduce the symptoms of synucleopathies like PD, which are affecting mainly intracellular processes leading to the typical symptoms described below. It is even more surprising as it is currently believed that the overlapping effects of both molecules are caused by direct interactions of the two proteins which should mainly occur intracellularly.

According to the present invention the term "synucleinopathy" includes all neurodegenerative disorders characterized by pathological synuclein aggregations. Several neurodegenerative disorders including Parkinson's Disease (PD), Lewy Body Disease (LBD), Diffuse Lewy Body Disease (DLBD), Dementia with Lewy Bodies (DLB), Parkinsonism with Dementia (PDD), Multiple System Atrophy (MSA) and Neurodegeneration with Brain Iron Accumulation type I (NBIA Type I) are collectively grouped as synucleinopathies.

"Symptoms of synucleopathy", as used herein, refers to those symptoms of the synucleopathies, in particular Parkinson's disease, which affect the motor and non-motor behaviour of a patient suffering from said disease. "Motor symptoms" include resting tremor, Bradykinesia, rigidity, postural instability, stooped posture, dystonia, fatigue, impaired fine motor dexterity and motor coordination, impaired gross motor coordination, poverty of movement (decreased arm swing), akathisia, speech problems, such as softness of voice or slurred speech caused by lack of muscle control, loss of facial expression, or "masking", micrographia, difficulty swallowing, sexual dysfunction, drooling etc. "Non-motor" symptoms include pain, dementia or confusion, sleep disturbances, constipation, skin problems, depression, fear or anxiety, memory difficulties and slowed thinking, urinary problems, fatigue and aching, loss of energy, compulsive behaviour, cramping etc.

According to a preferred embodiment of the present invention the synucleopathy is selected from the group of Parkinson's Disease, Dementia with Lewy Bodies, multiple system atrophy and neurodegeneration with brain iron accumulation. Particularly preferred is Parkinson's disease.

Another aspect of the present invention relates to a peptide having or consisting of an amino acid sequence selected from the group consisting of SHTRLYF(C) (SEQ ID NO: 59), SGEYVFH(C) (SEQ ID NO: 66), SGQLKFP(C) (SEQ ID NO: 67), SGQIWFR(C) (SEQ ID NO: 68), SGEIHFN(C) (SEQ ID NO: 69), GQIWFIS(C) (SEQ ID NO: 76), NDAKIVF(C) (SEQ ID NO: 104), GQIIFQS(C) (SEQ ID NO: 77), GQIRFDH(C) (SEQ ID NO: 78), HMRLFFN(C) (SEQ ID NO: 60), GEMWFAL(C) (SEQ ID NO: 79), GELQFPP(C) (SEQ ID NO: 80), GELWFP(C) (SEQ ID NO: 70), SHQRLWF(C) (SEQ ID NO: 61), HQKMIFA(C) (SEQ ID NO: 62), GEMQFFI(C) (SEQ ID NO: 81), GELYFRA(C) (SEQ ID NO: 82), GEIRFAL(C) (SEQ ID NO: 83), GMIVFPH(C) (SEQ ID NO: 84), GEIWFEG(C) (SEQ ID NO: 71), GEIYFER(C) (SEQ ID NO: 72), AIPLFVM(C) (SEQ ID NO: 101), GDLKFPL(C) (SEQ ID NO: 85), GQILFPV(C) (SEQ ID NO: 86), GELFFPK(C) (SEQ ID NO: 87), GQIMFPR(C) (SEQ ID NO: 88), HMRMYFE(C) (SEQ ID NO: 63), GSLFFWP(C) (SEQ ID NO: 89), GEILFGM(C) (SEQ ID NO: 90), GQLKFPF(C) (SEQ ID NO: 91), KLPLFVM(C) (SEQ ID NO: 102), GTIFFRD(C) (SEQ ID NO: 92), THQRLWF(C) (SEQ ID NO: 64), GQIKFAQ(C) (SEQ ID NO: 93), GTLIFHH(C) (SEQ ID NO: 94), GEIRFGS(C) (SEQ ID NO: 73), GQIQFPL(C) (SEQ ID NO: 95), GEIKFDH(C) (SEQ ID NO: 74), GEIQFGA(C) (SEQ ID NO: QLPLFVL(C) (SEQ ID NO: 103), HQKMIF(C) (SEQ ID NO: 65), GELFFEK(C) (SEQ ID NO: 96), GEIRFEL(C) (SEQ ID NO: 97), AcGEIYFER(C) (SEQ ID NO: 105), SGEIYFER(C) (SEQ ID NO: 98), AGEIYFER(C) (SEQ ID NO: 99) and (C)GEIYFER (SEQ ID NO: 100). As indicated by the use of the parenthesis the peptides of the present invention may or may not comprise the cysteine residue at the C- or N-terminus. Consequently the present invention encompasses also the following amino acid sequences: SHTRLYF (SEQ ID NO: 107), SGEYVFH (SEQ ID NO: 108), SGQLKFP (SEQ ID NO: 109), SGQIWFR (SEQ ID NO: 110), SGEIHFN (SEQ ID NO: 111), GQIWFIS (SEQ ID NO: 112), NDAKIVF (SEQ ID NO: 113), GQIIFQS (SEQ ID NO: 114), GQIRFDH (SEQ ID NO: 115), HMRLFFN (SEQ ID NO: 116), GEMWFAL (SEQ ID NO: 117), GELQFPP (SEQ ID NO: 118), GELWFP (SEQ ID NO: 119), SHQRLWF (SEQ ID NO: 120), HQKMIFA (SEQ ID NO: 121), GEMQFFI (SEQ ID NO: 122), GELYFRA (SEQ ID NO: 123), GEIRFAL (SEQ ID NO: 124), GMIVFPH (SEQ ID NO: 125), GEIWFEG (SEQ ID NO: 126), GEIYFER (SEQ ID NO: 127), AIPLFVM (SEQ ID NO: 128), GDLKFPL (SEQ ID NO: 129), GQILFPV (SEQ ID NO: 130), GELFFPK (SEQ ID NO: 131), GQIMFPR (SEQ ID NO: 132), HMRMYFE (SEQ ID NO: 133), GSLFFWP (SEQ ID NO: 134), GEILFGM (SEQ ID NO: 135), GQLKFPF (SEQ ID NO: 136), KLPLFVM (SEQ ID NO: 137), GTIFFRD (SEQ ID NO: 138), THQRLWF (SEQ ID NO: 139), GQIKFAQ (SEQ ID NO: 140), GTLIFHH (SEQ ID NO: 141), GEIRFGS (SEQ ID NO: 142), GQIQFPL (SEQ ID NO: 143), GEIKFDH (SEQ ID NO: 144), GEIQFGA (SEQ ID NO: 145), QLPLFVL (SEQ ID NO: 146), HQKMIF (SEQ ID NO: 147), GELFFEK (SEQ ID NO: 148), GEIRFEL (SEQ ID NO: 149), SGEIYFER (SEQ ID NO: 150), and AGEIYFER (SEQ ID NO: 151).

According to a preferred embodiment the peptide is coupled to a pharmaceutically acceptable carrier, preferably KLH (Key-hole Limpet Hemocyanin).

Yet another aspect of the present invention relates to a pharmaceutical formulation, preferably a vaccine, comprising at least one peptide according to the present invention. Said pharmaceutical formulation may be employed to treat individuals suffering from Alzheimer's disease or prevent the formation of Aβplaques in an individual to impede the formation of Alzheimer's disease.

The present invention is further illustrated by the following figures and examples, however without being restricted thereto.

Figure 7:
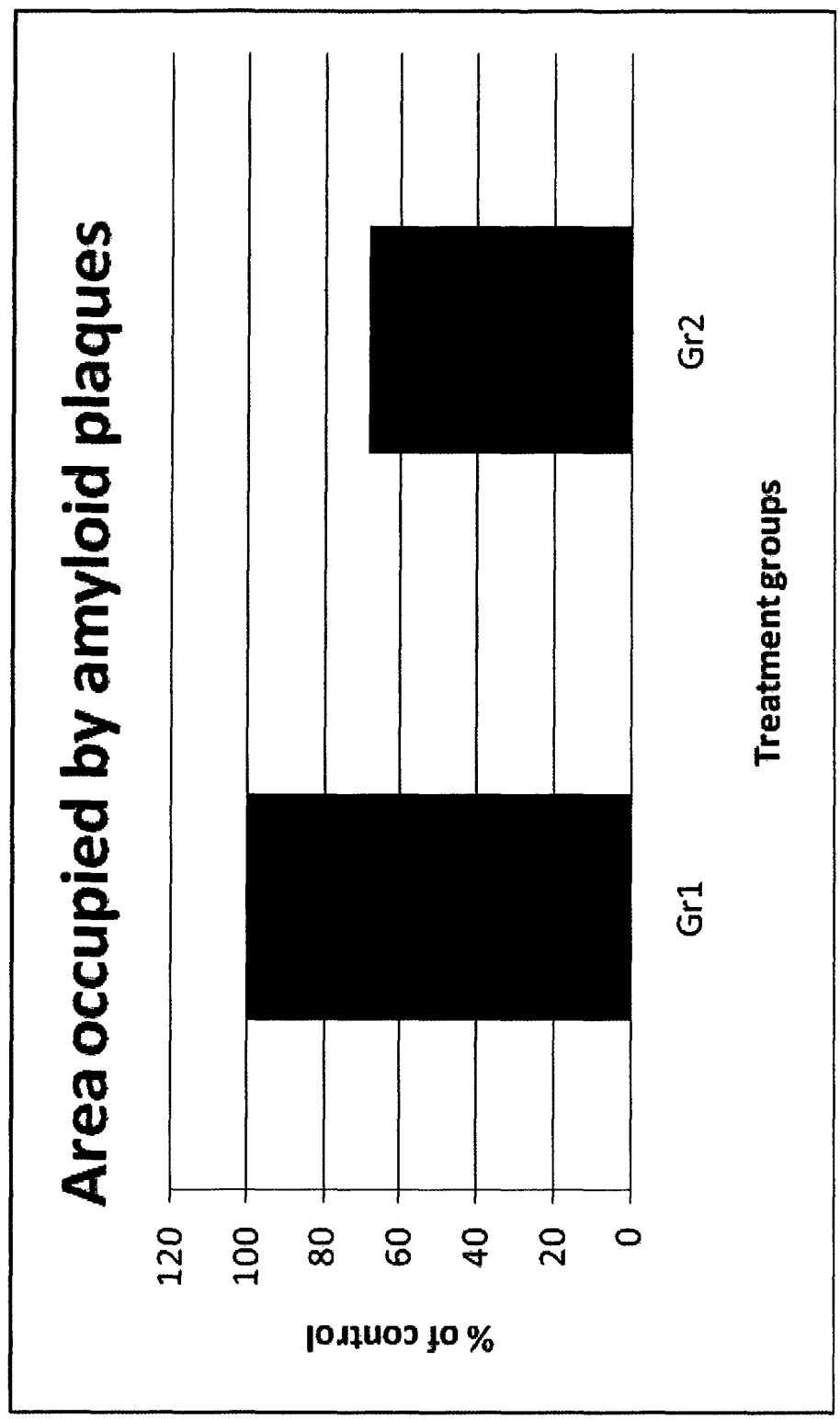

FIG. 7 shows areas occupied by amyloid plaques. Tg2576 were injected 6 times with mimotope vaccines adjuvanted with aluminium hydroxide (ALUM) by s.c. inoculation at monthly intervals. Control mice received PBS-ALUM only. Area occupied by amyloid plaques shown as percent of the control group. Gr1 . . . control group; Gr2 . . . received p4675.

EXAMPLES

Methods

The antibodies used for the mimotope identification according to the present invention detect amino acid sequences derived from human Aβ but do not bind to full length human APP. The sequences detected include EVHHQKLVFFAED (=original epitope aa11-24 of Aβ) (SEQ ID NO: 152) and p(E)VHHQKLVF (p4374=original epitope aa11-19 of Aβ with a pyroglutamate modification at the N-Terminus) (SEQ ID NO: 153). The antibody may be a monoclonal or polyclonal antibody preparation or any antibody part or derivative thereof, the only prerequisite is that the antibody molecule specifically recognises at least one of the epitopes mentioned above (derived from human Aβ), but does not bind to full length human APP.

The mimotopes are identified and further characterised with such monoclonal antibodies and peptide libraries.

Example 1

Generation of Monoclonal Antibodies to Specifically Detect β-Amyloid and N-Terminally Truncated and/or Post-Translationally Modified β-Amyloid Fragments A monoclonal antibody derived from the fusion of experiment Alz-9 was generated: C57/B16 mice were immunized repeatedly with original Aβ epitope HQKLVFC (SEQ ID NO: 154) coupled to KLH (Keyhole Limpet Hemocyanin) and Alum (Aluiminium Hydroxide) as adjuvant. p4377 peptide-specific, antibody-producing hybridomas were detected by ELISA (p4377-peptide-coated ELISA plates). Human Aβ40/42 (recombinant protein) was used as positive control peptide: hybridomas recognizing the recombinant protein immobilised on ELISA plates were included because they were binding both peptide and full length Aβ specifically. p1454 (Human Aβ 33-40) was used as negative control peptide. Furthermore hybridomas were tested against p4374, p1323 and sAPP-alpha. Only hybridomas with good p4374, and p1323 binding and a lack of sAPP-alpha binding were used for further antibody development.

The Hybridoma clone MV-002 (internal name A115; IgG2b) was purified and analysed for specific detection of p1323, p4374, p4377, p1454, Aβ and sAPP-alpha respectively. MV-002 recognized the epitopes p1323 as well as p4377 and full length Aβ protein (recombinant protein; obtained from Bachem A G, Bubendorf, Switzerland) in ELISA. It however did not detect p1454 in ELISA. Furthermore, the MV-002 antibodies failed to detect sAPP-alpha but bound specifically to the peptide p4374 encoding the pyroglutamate version of Aβ11-19.

Example 2

Phage Display, in Vitro Binding and Inhibition ELISA

Phage Display libraries used in this example were: Ph.D. 7: New England BioLabs E8102L (linear 7mer library). Phage Display was done according to manufacturer's protocol (www.neb.com).

After 2 or 3 subsequent rounds of panning, single phage clones were picked and phage supernatants were subjected to ELISA on plates coated with the antibody that was used for the panning procedure. Phage clones that were positive in this ELISA (strong signal for the target, but no signal for unspecific control) were sequenced. From DNA sequences, peptide sequences were deduced. These peptides were synthesized and characterised in binding and inhibition ELISA. Additionally, some novel mimotopes were created by combining sequence information from mimotopes identified in the screen to support the identification of a consensus sequence for a mimotope vaccination.

1. In Vitro Binding Assay (ELISA)

Peptides derived from Phage Display as well as variants thereof were coupled to BSA and bound to ELISA plates (1 µM; as indicated in the respective figures) and subsequently incubated with the monoclonal antibody that was used for the screening procedure to analyse binding capacity of identified peptides.

2. In Vitro Inhibition Assay (ELISA)

Different amounts of peptides (concentrations ranging from 5 µg to 0.03 µg; serial dilutions), derived from Phage Display were incubated with the monoclonal antibody that was used for the screening procedure. Peptides diminishing subsequent binding of the antibody to the original epitope coated on ELISA plates were considered as inhibiting in this assay.

Example 3

In Vivo Testing of Mimotopes: Analysis of Immunogenicity and Crossreactivity

1. In Vivo Testing of Mimotopes

Inhibiting as well as non-inhibiting peptides were coupled to KLH and injected into mice (wildtype C57/Bl6 mice; subcutaneous injection into the flank) together with an appropriate adjuvant (aluminium hydroxide). Animals were vaccinated 3-6 times in biweekly intervals and sera were taken biweekly as well. Titers to injected peptides, as well as to an irrelevant peptide were determined with every serum. Furthermore, titers against the recombinant human Aβ protein, and against original peptides were determined respectively. In general sera were analysed by reaction against peptides coupled to Bovine Serum Albumin (BSA) and recombinant full length proteins which were immobilised on ELISA plates. Titers were determined using anti mouse IgG specific antibodies. For detailed results see FIGS. 4, 5 and 6 respectively.

Figure 1:
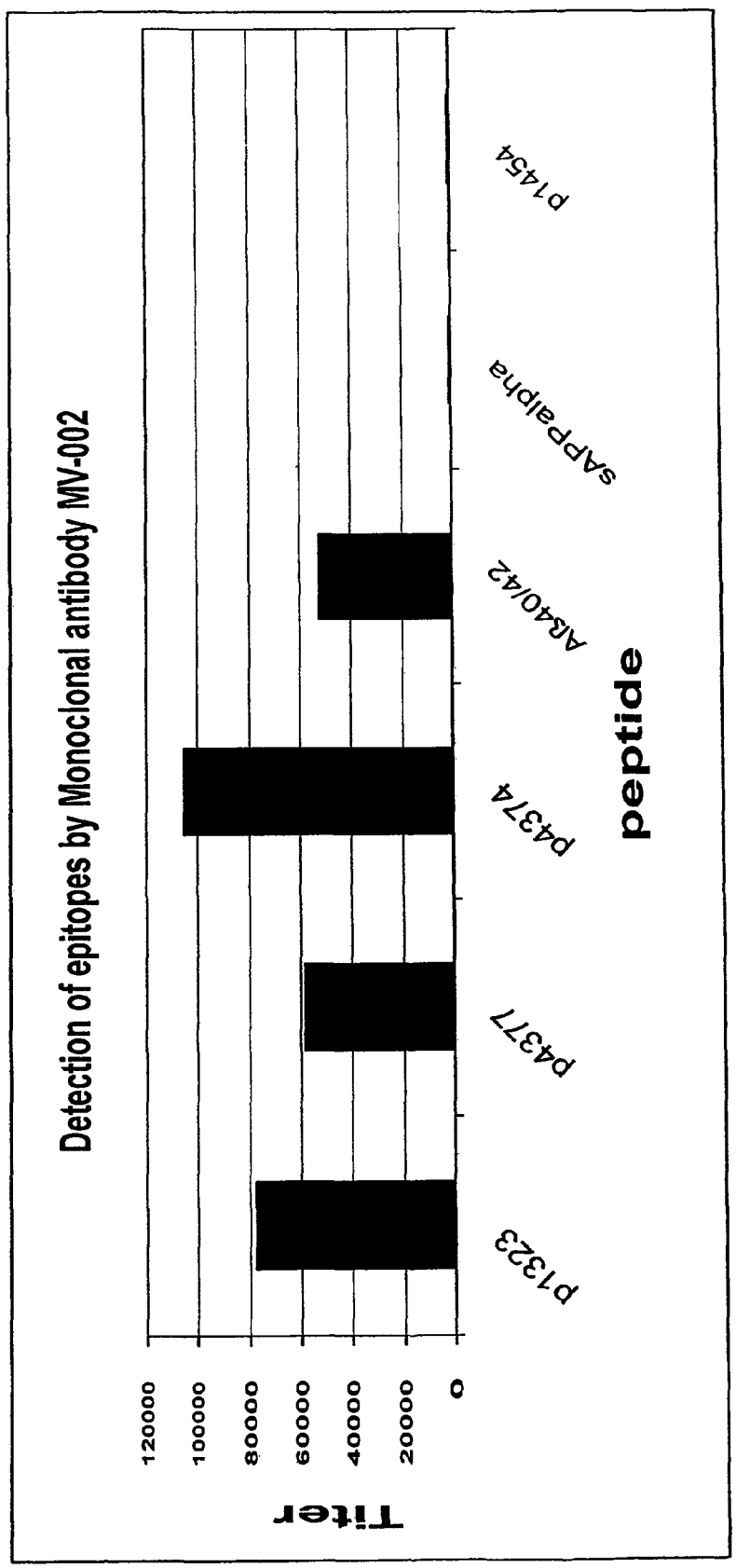
FIG. 1 shows binding of monoclonal antibody MV-002 to specific peptides and recombinant proteins.
Figure 2:
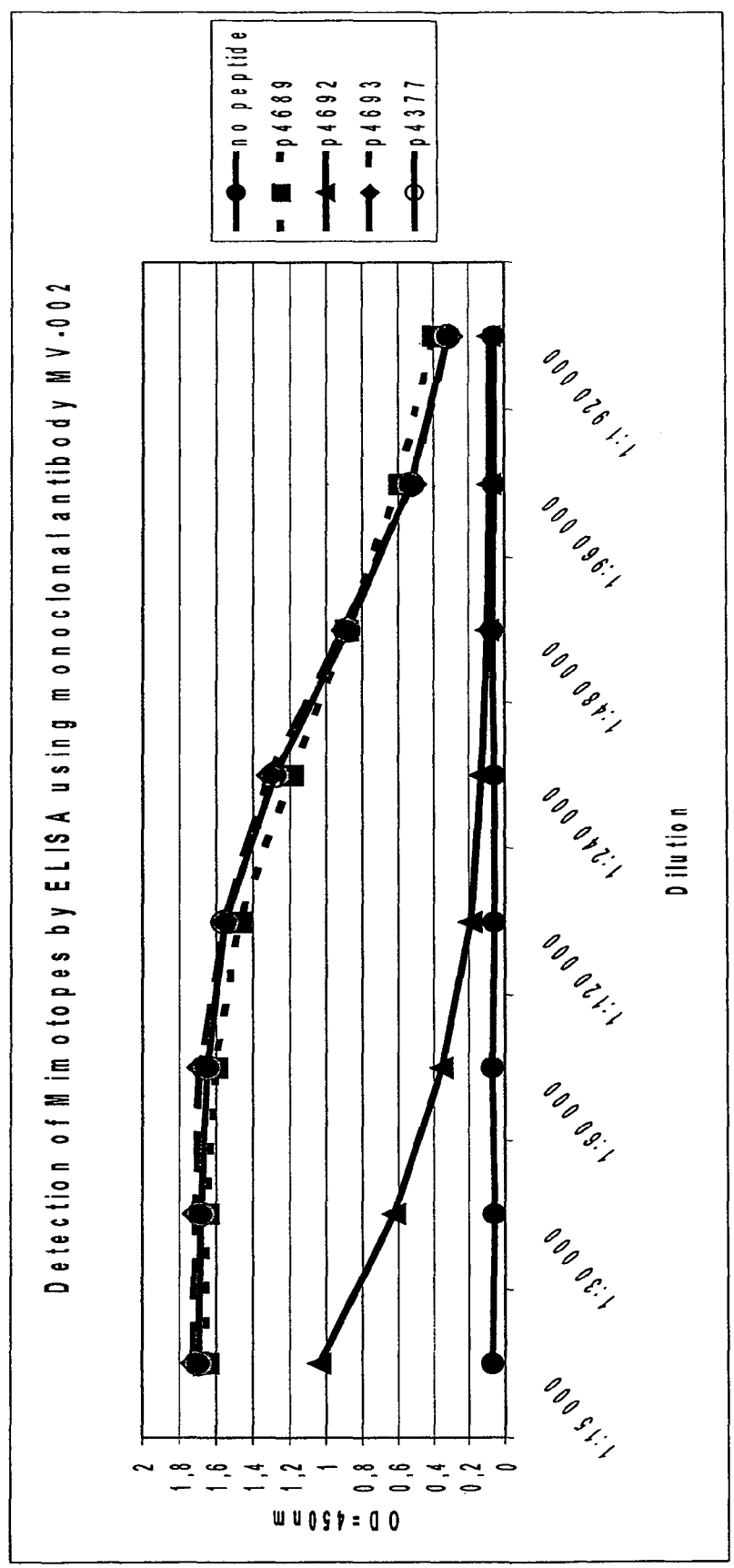
FIG. 2 shows typical binding assays with mimotopes for βamyloid and N-terminally truncated and/or posttranslationally modified β-amyloid fragments.
Figure 3:
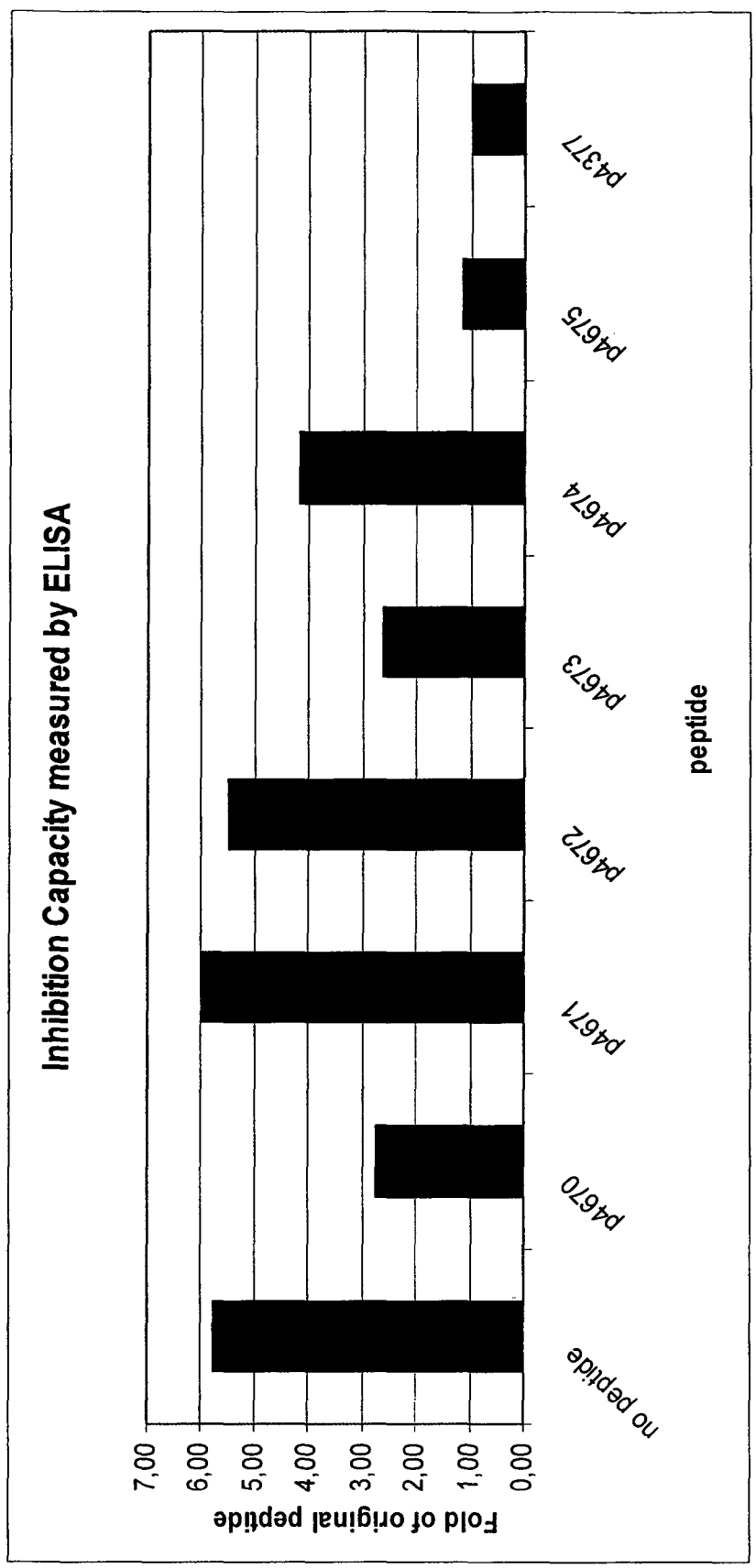
FIG. 3 shows typical inhibition assays with mimotopes for βamyloid and N-terminally truncated and/or posttranslationally modified β-amyloid fragments.

2. Results 2.1. Identification of Specific Monoclonal Antibodies (mAB) Directed Against N-Terminally Truncated and Modified Forms of Aβ:

FIG. 1 depicts the characterisation of the monoclonal antibody MV-002 (internal name A115; IgG2b) derived from experiment Alz-9 demonstrating specificity for full length Aβ and Aβ fragments truncated at position E11 and H14 and modified at position E11 to pE11.

2.2. Screening with Specific mABs Directed Against N-Terminally Truncated and Modified Forms of Aβ:

2.2.1. Phage Display Library Ph.D. 7

2.2.1.1. Screening with Monoclonal Antibody Directed Against p1323

47 Sequences were identified by screening PhD 7 phage display libraries in this screen: Table 1 summarises the peptides identified and their binding capacity as compared to the original epitope.

TABLE 1 mimotopes binding to the parental antibody MV-002

| Internal Peptide number | SEQ ID No. | Sequence | Binding Capacity |
|---|---|---|---|
| p4403 | 1 | SHTRLYFC | 1 |
| p4404 | 2 | SGEYVFHC | 1 |
| p4413 | 3 | SGQLKFPC | 1 |
| p4414 | 4 | SGQIWFRC | 1 |
| p4415 | 5 | SGEIHFNC | 1 |
| p4666 | 6 | GQIWFISC | 1 |
| p4667 | 7 | NDAKIVFC | 3 |
| p4668 | 8 | GQIIFQSC | 2 |
| p4669 | 9 | GQIRFDHC | 3 |
| p4670 | 10 | HMRLFFNC | 3 |
| p4671 | 11 | GEMWFALC | 3 |
| p4672 | 12 | GELQFPPC | 3 |
| p4673 | 13 | GELWFPC | 3 |
| p4674 | 14 | SHQRLWFC | 3 |
| p4675 | 15 | HQKMIFAC | 3 |
| p4676 | 16 | GEMQFFIC | 3 |
| p4677 | 17 | GELYFRAC | 3 |
| p4678 | 18 | GEIRFALC | 3 |
| p4679 | 19 | GMIVFPHC | 3 |
| p4680 | 20 | GEIWFEGC | 3 |
| p4681 | 21 | GEIYFERC | 3 |
| p4682 | 22 | AIPLFVMC | 1 |
| p4683 | 23 | GDLKFPLC | 3 |

TABLE 1-continued mimotopes binding to the parental antibody MV-002

Figure 4:
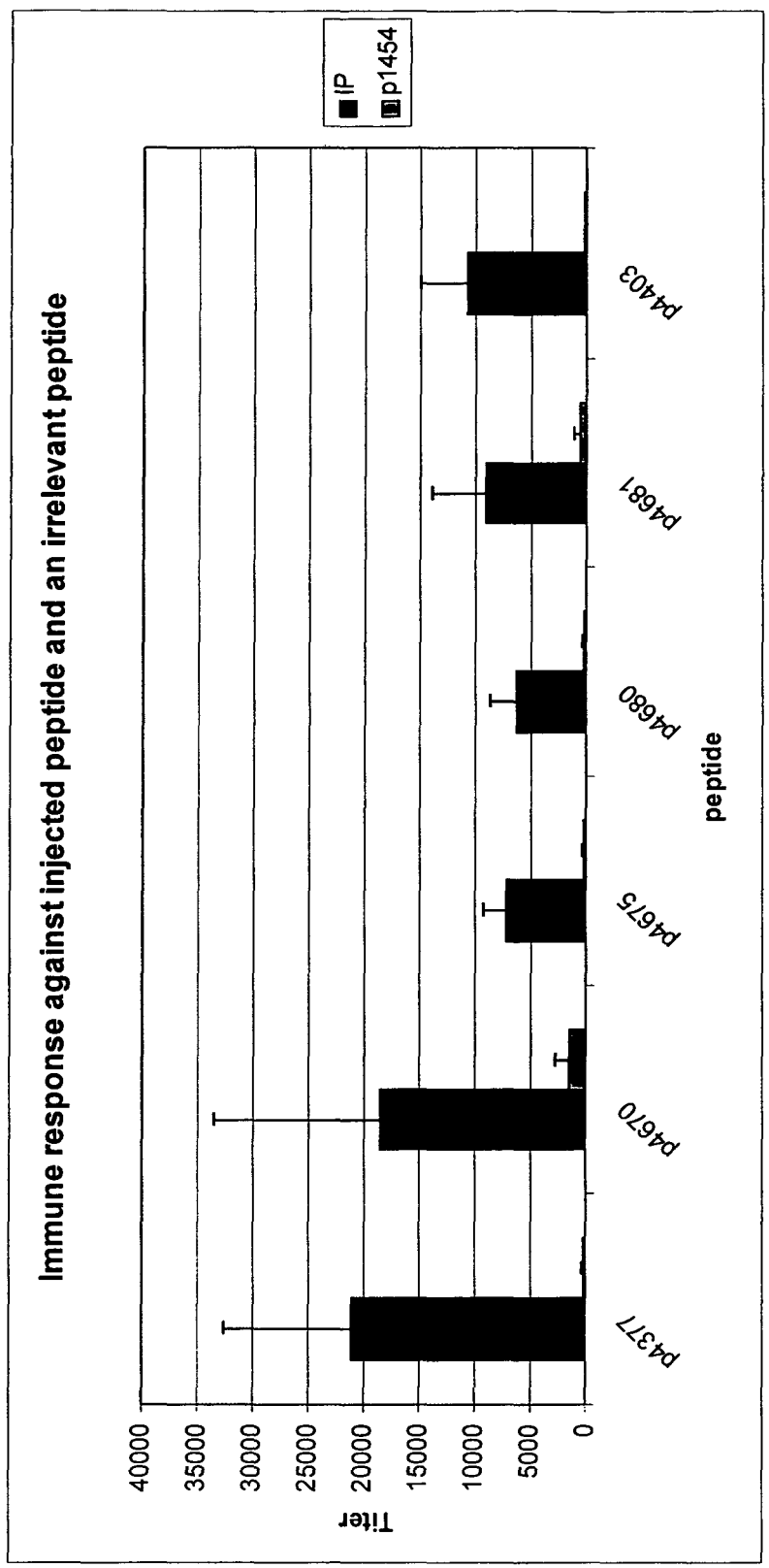
FIG. 4 shows examples for in vivo characterisations of the immune response elicited by mimotope vaccination (injected peptide/irrelevant peptide).
Figure 5:
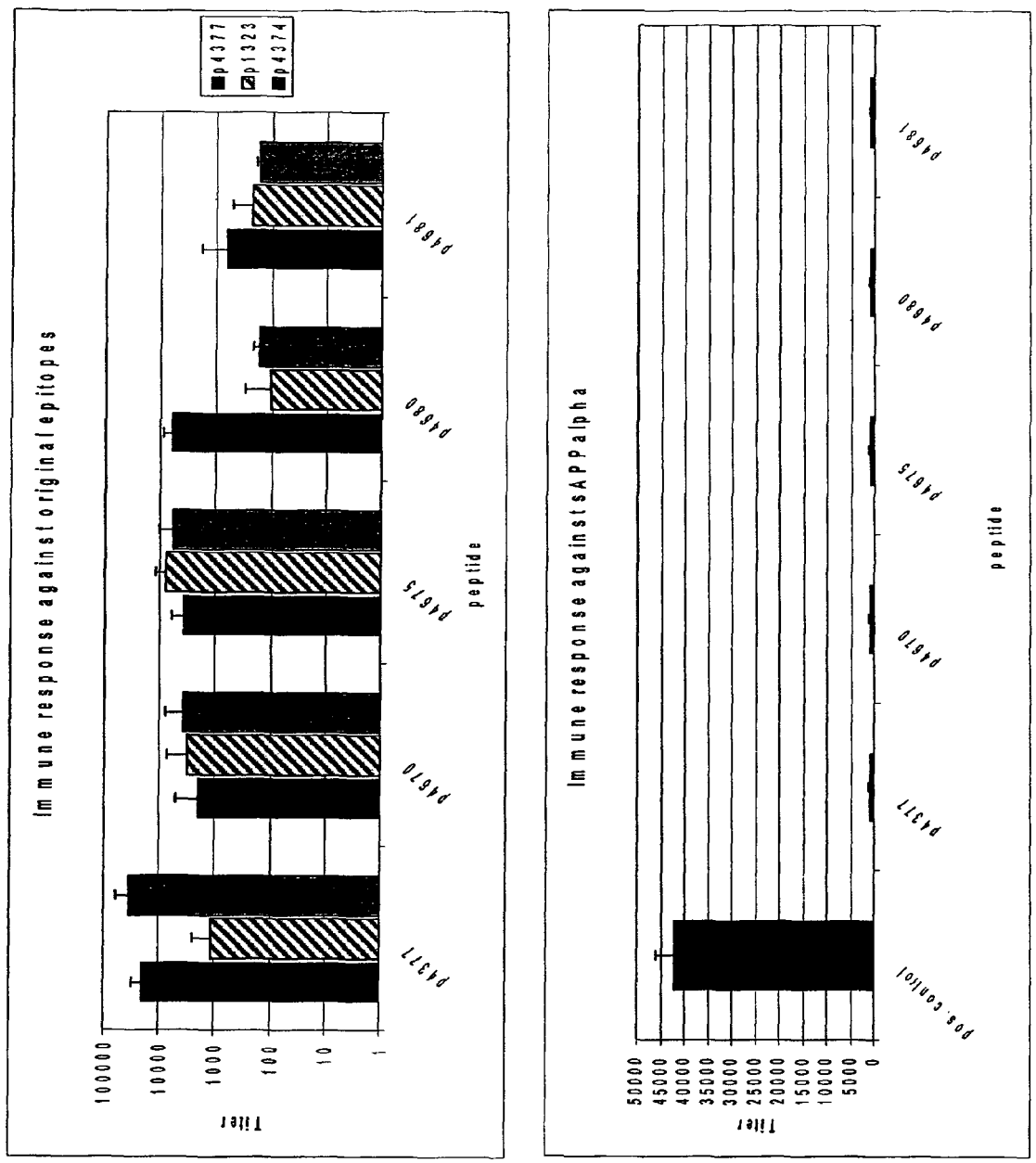
FIG. 5 shows examples for in vivo characterisation of the immune response elicited by mimotope vaccination against Amyloid Beta fragments and sAPP-alpha.
Figure 6:
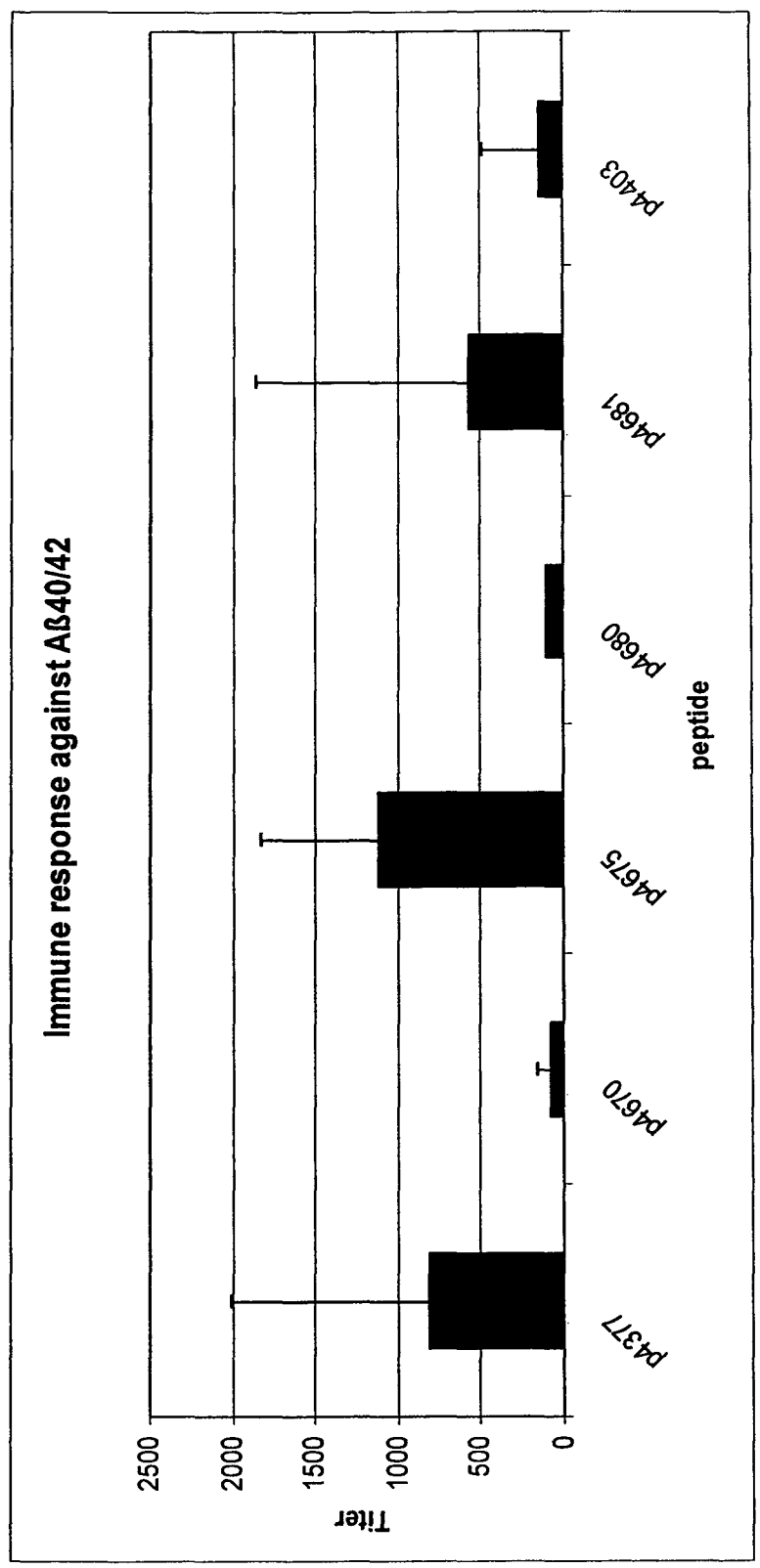
FIG. 6 shows examples for in vivo characterisation of the immune response elicited by mimotope vaccination against full length Aβ40/42.

| Internal Peptide number | SEQ ID No. | Sequence | Binding Capacity |
|---|---|---|---|
| p4684 | 24 | GQILFPVC | 3 |
| p4685 | 25 | GELFFPKC | 3 |
| p4686 | 26 | GQIMFPRC | 3 |
| p4687 | 27 | HMRMYFEC | 3 |
| p4688 | 28 | GSLFFWPC | 2 |
| p4689 | 29 | GEILFGMC | 3 |
| p4690 | 30 | GQLKFPFC | 3 |
| p4691 | 31 | KLPLFVMC | 1 |
| p4692 | 32 | GTIFFRDC | 1 |
| p4693 | 33 | THQRLWFC | 3 |
| p4694 | 34 | GQIKFAQC | 3 |
| p4695 | 35 | GTLIFHHC | 2 |
| p4696 | 36 | GEIRFGSC | 3 |
| p4697 | 37 | GQIQFPLC | 3 |
| p4698 | 38 | GEIKFDHC | 3 |
| p4699 | 39 | GEIQFGAC | 3 |
| p4700 | 40 | QLPLFVLC | 1 |
| p4794 | 41 | HQKMIFC | 2 |
| p4795 | 42 | GELFFEKC | 2 |
| p4796 | 43 | GEIRFELC | 2 |
| p4804 | 44 | Ac-GEIYFERC | 2 |
| p4805 | 45 | SGEIYFERC | 1 |
| p4806 | 46 | AGEIYFERC | 1 |
| p4807 | 47 | CGEIYFER | 1 |

Legend to Table 1:
the binding capacity is coded by the following binding code: 1:X describes the dilution factor of the parental AB. Ac- . . . indicates acetylated AA.

| binding code | | OD halfmax 1:X |
|---|---|---|
| 0 | no binding | :0 |
| 1 | weak binding | :<40000 |
| 2 | medium binding | :40000-320000 |
| 3 | strong binding | :>320000 |

2.3. In Vitro Characterisation of Mimotopes Identified in Screening Phage Display Libraries with Monoclonal Antibodies Directed Against N-Terminally Truncated and Modified Forms of Aβ:

FIGS. 2 and 3 show representative examples for binding and inhibition assays used to characterise mimotopes in vitro. Data obtained are summarised in Tables 1 and 2 respectively.

MV-002 Mimotopes: From the 47 sequences presented 11 sequences inhibited binding of the monoclonal antibody MV-002 in in vitro competition experiments. Additional 36 sequences were identified that did not inhibit binding of monoclonal antibody in in vitro competition experiments but still retained binding capacity to the parental antibody (Table 2). Importantly, as described in FIGS. 4-6, the ability to compete with the original epitope for binding to the parental antibody in vitro was no prerequisite to mount specific immune responses cross reacting with specific peptides in vivo. Thus inhibiting as well as non-inhibiting peptides can be used for inducing immune responses detecting peptides in vivo (for details see: FIGS. 4-6) which can lead to clearance of amyloid peptides from the brain.

TABLE 2 mimotopes identified in this invention giving positive results in inhibiting assays; MV-002 Mimotopes

| Internal Peptide number | SEQ ID No. | Sequence | Inhibition Capacity |
|---|---|---|---|
| p4667 | 7 | NDAKIVFC | 1 |
| p4670 | 10 | HMRLFFNC | 1 |
| p4673 | 13 | GELWFPC | 1 |
| p4674 | 14 | SHQRLWFC | 1 |
| p4675 | 15 | HQKMIFAC | 2 |
| p4680 | 20 | GEIWFEGC | 2 |
| p4681 | 21 | GEIYFERC | 2 |
| p4689 | 29 | GEILFGMC | 1 |
| p4698 | 38 | GEIKFDHC | 2 |
| p4699 | 39 | GEIQFGAC | 1 |
| p4794 | 41 | HQKMIFC | 1 |

Legend to Table 2:
the inhibition capacity is coded by the following code: Weak inhibition means more peptide is required to lower AB binding than with the original epitope; strong inhibition means similar peptide amounts are required for mimotope and original epitope for lowering AB binding. Mimotopes are compared to the original peptide as standard. OD at 5 ug peptide used in the assay is used to calculate the competition capacity compared to original peptide.
competition code

| | |
|---|---|
| 0 | no inhibition (OD of peptide above 4, 6 times of original peptide) |
| 1 | Weaker than original epitope (OD of peptide below 4, 6 times of original peptide) |
| 2 | strong inhibition (as original epitope; OD of peptide below 2, 3 times of original peptide) |

2.4. In Vivo Characterisation of Mimotopes Identified in Screening Phage Display Libraries with a Monoclonal Antibody Directed Against Amyloid Beta:

Female C57/b16 mice, 5-6 mice per group, were subcutaneously immunized with 30 μg peptide coupled to KLH. Control groups were administered original epitope-KLH conjugates respectively. As adjuvant alum was used (always 1 mg per mouse). The peptides administered were all able to bind to monoclonal antibodies specifically although some of the peptides did not inhibit the binding of the original epitope to its parental antibody in vitro (in an in vitro inhibition assay). The in vitro ELISA assay to determine the antibody titer was performed with sera of single mice after each vaccination in a two week interval (see FIGS. 6 and 7 respectively). Titers were calculated as OD max/2 in all figures shown. The wells of the ELISA plate were coated with mimotope-BSA conjugate and an irrelevant peptide-BSA conjugate (negative control). The positive control was performed by reaction of the parental antibody with the respective mimotope-BSA conjugate. The detection was performed with anti-mouse IgG. Additionally, recombinant proteins were immobilised on ELISA plates and sera reacted accordingly. FIGS. 4, 5 and 6 show representative examples for assays used to characterise mimotopes in vivo. The results depicted were derived from peptides active in in vitro inhibition assays like p4670, p4675, p4680, and p4681 and a peptide without inhibition capacity, p4403 respectively.

FIG. 4 shows examples for in vivo characterisations of the immune response elicited by mimotope vaccination by analysing the immune response against injected peptide and an irrelevant peptide, containing an unrelated sequence. In the examples shown, the epitope p4377 and the mimotopes p4670, p4675, p4680, p4681 and p4403 elicited immune responses against the injected peptides but failed to induce a relevant unspecific immune response against an unrelated sequence (p1454).

FIG. 5 shows examples for in vivo characterisations of the immune response elicited by mimotope vaccination against the respective original epitope of the parental antibody (p4377) as well as against peptides derived from truncated species of Aβ(p1323 and p4374) and against sAPP alpha.

p4377 and the mimotopes p4670, p4675, p4680, p4681 and p4403 mounted detectable immune responses against the original epitope p4377. A similar phenomenon could be detected analysing cross reactivity against the modified form as displayed by p4374. Interestingly, the original epitope and the mimotope vaccines mounted relevant titers against p4374 the modified form of the original epitope. Surprisingly, the mimotopes seemed to be able to induce but did not necessarily induce a more efficient immune response against p1323 indicating a potential to induce a broader immuno-reactivity as compared to the original Aβ fragment. Additionally, no reactivity was detectable against sAPP alpha.

FIG. 6 shows examples for in vivo characterisations of the immune response elicited by mimotope vaccination against full length Aβ. Surprisingly, the mimotopes selected by using MV-002 induced a cross reaction not only with the truncated or modified short epitopes used to create the antibodies but also induced cross reactivity to full length, non modified forms of Aβ as good as the original sequence or even more efficiently than p4377.

Interestingly competing as well as non competing peptides were able to induce similar immune responses specifically interacting with peptides containing original Aβ sequences. Thus the mimotopes presented in this invention constitute optimised, novel vaccine candidates to target a broad spectrum of naturally occurring forms of the Aβ peptides as have been found in the brain of AD patients. The forms include but are not limited to Aβ1-40/42, and N-terminally truncated forms like Aβ3-40/42, Aβ(pE)3-40/42, unmodified Aβ11-40/42, modified Aβp(E)11-40/42 and Aβ14-40/42 respectively. Importantly, the mimotopes presented also did not induce a cross reactivity to the neoepitopes present in sAPP alpha after cleavage from APP and thus do not interfere with normal sAPP alpha signalling (see FIG. 5 for details).

TABLE 3

Non-Mimotope peptides used

| Internal Peptide no. | SEQ ID No. | Sequence |
|---|---|---|
| p1253 | 48 | DAEFRHDSGYC |
| p1323 | 49 | CHQKLVFFAED |
| p4374 | 50 | p(E)VHHQKLVFC |
| p4377 | 51 | EVHHQKLVFC |
| p1454 | 52 | CGLMVGGVV |
| Aβ1-40 | 53 | DAEFRHDSGYEVHHQKLVFFAEDVGSNKGAI-IGLMVGGVV; derived from human APP (gi:112927) |
| Aβ1-42 | 54 | DAEFRHDSGYEVHHQKLVFFAEDVGSNKGAI-IGLMVGGVVIA; derived from human APP (gi:112927) |
| sAPPalpha | 55 | alpha-Secretase induced cleavage product derived from human APP (gi:112927) |

In Table 4 further examples of the immune response elicited by mimotope vaccination against full length Aβ by using MV-002 derived mimotopes are described. All peptides listed in table 4 mount specific immune reactions against full length and/or truncated and modified forms of Aβ or fragments thereof.

TABLE 4

In vivo characterisation of mimotopes: MV-002

| Internal Peptide number | SEQ ID No. | Detection of Aβ/truncated/modified forms |
|---|---|---|
| p4403 | 1 | + |
| p4404 | 2 | + |
| p4413 | 3 | + |
| p4414 | 4 | + |
| p4415 | 5 | + |
| p4670 | 10 | + |
| p4673 | 13 | + |
| p4675 | 15 | + |
| p4680 | 20 | + |
| p4681 | 21 | + |
| p4693 | 33 | + |
| p4696 | 36 | + |
| p4698 | 38 | + |
| p4699 | 39 | + |

2.5: In Vivo Characterisation of Mimotopes for the Efficacy to Reduce AD Like Disease in Transgenic Animals (Proof of Concept Analysis)

The Tg2576 AD mouse model was used to study the preclinical efficacy of the mimotope vaccines. This transgenic line is expressing human APP carrying the Swedish double mutation at aa position 670/671 under the control of a hamster prion protein (PrP) promoter which results in overexpression of the protein. It is currently one of the most widely employed models in AD research. The Tg2576 model recapitulates various hallmarks of AD pathology including disease-specific amyloid plaque deposition and astrocytosis. As all other AD model systems available to date, it does not reflect all cardinal neuropathological features of AD.

To assess whether treatment with mimotopes is capable of preventing cerebral Aβ accumulation, Tg2576 mice were s.c.

injected 6 times at monthly intervals with peptide-KLH conjugates adsorbed to ALUM (adjuvant: aluminium hydroxide) or PBS adsorbed to ALUM (referred to as PBS or control) alone. Up to eight weeks after the last immunization, animals were sacrificed, their brains harvested and analyzed for their Aβ load (AD-like pathology). The mice were sacrificed under deep anaesthesia. Subsequently, the brain was isolated, fixed in 4% PFA and dehydrated by graded Ethanol series followed by incubation in Xylene and paraffin embedding. Each paraffin-embedded brain was sectioned at 7 μM using a slicing microtome and sections were mounted on glass slides.

As a method to assay AD-like pathology in Tg2576 animals, we analyzed the relative area occupied by amyloid deposits in the brain of treated animals. This analysis was performed using an automated area recognition program. To identify the plaques, sections were stained with the monoclonal antibody (mAb) 3A5 (specific for Aβ40/42). Mimotope treated animals were compared to control animals. All animals have been sacrificed at an age of 13, 5-14 months. For this analysis 3 slides/animal covering the cortex and hippocampus were selected, stained with mAb 3A5 and subsequently documented using the Mirax-system (Zeiss). For the calculation of the area occupied by amyloid plaques, we analyzed up to four individual sections per slide and sections carrying tissue artifacts and aberrant staining intensities have been excluded after inspection of the result pictures.

For the mimotopes of MV002 we performed an area analysis using one exemplary candidate: Analysis was performed following repeated vaccination using peptide-KLH conjugate vaccines. The control group showed an average occupation of 0.35% as compared to 0.24% for the mimotope treated animals respectively. This corresponds to a reduction following mimotope treatment of 31% in group 2.

Thus, this set of data clearly indicates a beneficial effect of mimotope vaccine treatment on AD like pathology in transgenic animals.

The invention claimed is:

1. An isolated peptide consisting of an amino acid sequence selected from the group consisting of SHTRLYF(C) (SEQ ID NO: 59), SGEYVFH(C) (SEQ ID NO: 66), SGQLKFP(C) (SEQ ID NO: 67), SGQIWFR(C) (SEQ ID NO: 68), SGEIHFN(C) (SEQ ID NO: 69), GQIWFIS(C) (SEQ ID NO: 76), NDAKIVF(C) (SEQ ID NO: 104), GQIIFQS(C) (SEQ ID NO: 77), GQIRFDH(C) (SEQ ID NO: 78), HMRLFFN(C) (SEQ ID NO: 60), GEMWFAL(C) (SEQ ID NO: 79), GELQFPP(C) (SEQ ID NO: 80), GELWFP(C) (SEQ ID NO: 70), SHQRLWF(C) (SEQ ID NO: 61), HQKMIFA(C) (SEQ ID NO: 62), GEMQFFI(C) (SEQ ID NO: 81), GELYFRA(C) (SEQ ID NO: 82), GEIRFAL(C) (SEQ ID NO: 83), GMIVFPH(C) (SEQ ID NO: 84), GEIWFEG(C) (SEQ ID NO: 71), GEIYFER(C) (SEQ ID NO: 72), AIPLFVM(C) (SEQ ID NO: 101), GDLKFPL(C) (SEQ ID NO: 85), GQILFPV(C) (SEQ ID NO: 86), GELFFPK(C) (SEQ ID NO: 87), GQIMFPR(C) (SEQ ID NO: 88), HMRMYFE(C) (SEQ ID NO: 63), GSLFFWP(C) (SEQ ID NO: 89), GEILFGM(C) (SEQ ID NO: 90), GQLKFPF(C) (SEQ ID NO: 91), KLPLFVM(C) (SEQ ID NO: 102), GTIFFRD(C) (SEQ ID NO: 92), THQRLWF(C) (SEQ ID NO: 64), GQIKFAQ(C) (SEQ ID NO: 93), GTLIFHH(C) (SEQ ID NO: 94), GEIRFGS(C) (SEQ ID NO: 73), GQIQFPL(C) (SEQ ID NO: 95), GEIKFDH(C) (SEQ ID NO: 74), GEIQFGA(C) (SEQ ID NO: 75), QLPLFVL(C) (SEQ ID NO: 103), HQKMIF(C) (SEQ ID NO: 65), GELFFEK(C) (SEQ ID NO: 96), GEIRFEL(C) (SEQ ID NO: 97), AcGEIYFER(C) (SEQ ID NO: 105), SGEIYFER(C) (SEQ ID NO: 98), AGEIYFER(C) (SEQ ID NO: 99) and (C)GEIYFER (SEQ ID NO: 100).

2. The isolated peptide according to claim 1, which further comprises Keyhole Limpet Hemocyanin (KLH) coupled thereto.

3. A formulation, comprising at least one peptide according to claim 1 or 2 and a pharmaceutically acceptable carrier.

4. A method of treating β-amyloidoses in an subject in need thereof, the method comprising administering to the subject at least one compound comprising a peptide having an amino acid sequence selected from the group consisting of SGEYVFH(C) (SEQ ID NO: 66), SGQLKFP(C) (SEQ ID NO: 67), SGQIWFR(C) (SEQ ID NO: 68), SGEIHFN(C) (SEQ ID NO: 69), GQIWFIS(C) (SEQ ID NO: 76), GQIIFQS (C) (SEQ ID NO: 77), GQIRFDH(C) (SEQ ID NO: 78), GEMWFAL(C) (SEQ ID NO: 79), GELQFPP(C) (SEQ ID NO: 80), GELWFP(C) (SEQ ID NO: 70), GEMQFFI(C) (SEQ ID NO: 81), GELYFRA(C) (SEQ ID NO: 82), GEIRFAL(C) (SEQ ID NO: 83), GMIVFPH(C) (SEQ ID NO: 84), GEIWFEG(C) (SEQ ID NO: 71), GQILFPV(C) (SEQ ID NO: 86), GELFFPK(C) (SEQ ID NO: 87), GQIMFPR(C) (SEQ ID NO: 88), GSLFFWP(C) (SEQ ID NO: 89), GEILFGM(C) (SEQ ID NO: 90), GQLKFPF(C) (SEQ ID NO: 91), GTIFFRD(C) (SEQ ID NO: 92), GQIKFAQ(C) (SEQ ID NO: 93), GTLIFHH(C) (SEQ ID NO: 94), GEIRFGS(C) (SEQ ID NO: 73), GQIQFPL(C) (SEQ ID NO: 95), GEIKFDH(C) (SEQ ID NO: 74), GEIQFGA(C) (SEQ ID NO: 75), GELFFEK(C) (SEQ ID NO: 96), GEIRFEL(C) (SEQ ID NO: 97), GEIYFER(C) (SEQ ID NO: 72), SGEIYFER(C) (SEQ ID NO: 98), AGEIYFER(C) (SEQ ID NO: 99) and (C)GEIYFER (SEQ ID NO: 100),
    wherein said compound having a binding capacity to an antibody which is specific for an epitope of the amyloid-beta-peptide (Aβ) comprising the amino acid sequence HQKLVF (SEQ ID NO: 57) and/or HQKLVFFAED (SEQ ID NO: 58).

\* \* \* \* \*